(12) United States Patent
Krause et al.

(10) Patent No.: US 8,236,937 B2
(45) Date of Patent: Aug. 7, 2012

(54) METHODS AND COMPOSITIONS FOR THE DETECTION AND ISOLATION OF LIGANDS

(75) Inventors: Henry M. Krause, Mississauga (CA); Jens Tiefenbach, Toronto (CA)

(73) Assignee: InDanio Bioscience Inc., Toronto, Ontario (CA)

( * ) Notice: Subject to any disclaimer, the term of this patent is extended or adjusted under 35 U.S.C. 154(b) by 318 days.

(21) Appl. No.: 12/158,383

(22) PCT Filed: Dec. 22, 2006

(86) PCT No.: PCT/CA2006/002114
§ 371 (c)(1),
(2), (4) Date: Jun. 20, 2008

(87) PCT Pub. No.: WO2007/071062
PCT Pub. Date: Jun. 28, 2007

(65) Prior Publication Data
US 2008/0307534 A1  Dec. 11, 2008

Related U.S. Application Data

(60) Provisional application No. 60/752,365, filed on Dec. 22, 2005.

(51) Int. Cl.
*A01K 67/027* (2006.01)
(52) U.S. Cl. .................. 536/23.1; 800/3; 800/4
(58) Field of Classification Search .................. None
See application file for complete search history.

(56) References Cited

U.S. PATENT DOCUMENTS
6,380,458 B1  4/2002  Lin

FOREIGN PATENT DOCUMENTS
WO   WO 02/057792    7/2002
WO   WO 03/095619   11/2003
WO   WO03/095619  * 11/2003

OTHER PUBLICATIONS

Reinking et al. ("The *Drosophila* nuclear receptor E75 contains heme and is gas responsive." Cell. (Jul. 29, 2005). 122:195-207).*
Kozlova et al. (Development. 2002; 129: 739-1750).*
Zhang et al. (Biochemical and Biophysical Research Communications. 1996; 227: 707-711).*
Barolo et al. (Biotechniques, 2000; 29: 726, 728, 730, 732).*
Louie et al. (Nature Biotechnology. 2000; 18:321-325).*
Reinking, J., et al., "The *Drosophila* nuclear receptor E75 contains heme and is gas responsive", Cell, Jul. 29, 2005, pp. 195-207, vol. 122.
Kozlova, T., and Thummel, C.S., "Spatial patterns of ecdysteroid receptor activation during the onset of *Drosophila* metamorphosis", Development, 2002, pp. 1739-1750, vol. 129.
Osterwalder, T., et al., "A conditional tissue-specific transgene expression system using inducible GAL4", Proceedings of the National Academy of Sciences of the United States of America, 2001, pp. 12596-12601, vol. 98.

Mata De Urquiza, A., et al., "Feedback-inducible nuclear-receptor-driven reporter gene expression in transgenic mice", Proceedings of the National Academy of Sciences of the United States of America, 1999, pp. 13270-13275, vol. 96.
Han, D.D., et al., "Investigating the function of follicular subpopulations during *Drosophila* oogenesis through hormone-dependent enhancer-targeted cell ablation", Development, 2000, pp. 573-583, vol. 127.
Grover, G.S., et al. "Multiplexing nuclear receptors for agonist identification in a cell-based reporter gene high-throughput screen", Journal of Biomolecular Screening, 2003, pp. 239-246, vol. 8, No. 3.
Muddana, S.S., Peterson, B.R, Fluorescent cellular sensors of steroid receptor ligands, Chembiochem, 2003, pp. 848-855, vol. 4, No. 9.
Willson, T.M., Kliewer, S.A., "PXR, CAR and drug metabolism", Nature Reviews. Drug Discovery, Apr. 2002, pp. 259-266, vol. 1, No. 4.
Solomin, L., et al., "Retinoid-X receptor signalling in the developing spinal cord", Nature, Sep. 24, 1998, pp. 398-402, vol. 395.
Palanker, L., et al., "Dynamic regulation of *Drosophila* nuclear receptor activity in vivo", Development, Sep. 2006, pp. 3549-3562, vol. 133.
Barolo, S. et al., "GFP and beta-galactosidase transformation vectors for promoter/enhancer analysis in *Drosophila*", Biotechniques, 2000, pp. 726-732, vol. 29, No. 4.
Davidson, A.E. et al., Efficient gene delivery and gene expression in zebrafish using the *sleeping beauty* transposon, Development Biology, 2003, pp. 191-202, vol. 263.
Dhe-Paganon, S., et al., "Crystal structure of the HNF4α ligand binding domain in complex with endogenous fatty acid ligand", The Journal Biological Chemistry, 2002, pp. 37973-37976, vol. 277.
Dias, J. M., et al., "Genetic recombination as a reporter for screening steroid receptor agonists and antagonists", Analytical Biochemistry, 1998, vol. 258, pp. 96-102.
Glickman, J. F., et al., "A comparison of ALPHAScreen, TR-FRET, and TRF as assay methods for FXR nuclear receptors", Journal Biomolecular Screening, 2002, pp. 3-10, vol. 7, No. 1.
Hawkins, M. B., et al., "Identification of a third distinct estrogen receptor and reclassification of estrogen receptors in teleosts", Proc Natl Acad Sci USA, 2000, pp. 10751-10756, vol. 97, No. 20.
Köster, R. W., and Fraser, S. E., "Tracing transgene expression in living zebrafish embryos", Development Biology, 2001, pp. 329-346, vol. 233.
Shoji, W., et al., "Zebrafish semaphorin Z1a collapses specific growth cones and alters their pathway in vivo", Development, 1998, pp. 1275-1283, vol. 125.

(Continued)

*Primary Examiner* — Scott Long
(74) *Attorney, Agent, or Firm* — Bereskin & Parr LLP; Melanie Szweras

(57) ABSTRACT

A method for the detection and isolation of ligands, preferably nuclear receptor ligands, bound to their cognate receptors in live animals, is described. A novel composition comprising 1) a chimeric transcription factor containing a DNA-binding domain, preferably from a non-vertebrate transcription factor, fused to the ligand-binding domain (LBD) of a nuclear receptor, 2) a reporter system, driven by a promoter that contains binding sites for the chosen DNA-binding domain, 3) multiple affinity tags fused to the LBD fusion proteins to facilitate efficient purification, along with specifically associated molecules and 4) sequences required for simultaneous genomic integration of all three components above are described. To make use of the system, expression of the chimeric LBD protein is broadly induced.

28 Claims, 7 Drawing Sheets

OTHER PUBLICATIONS

Thermes, V., et al., "I-SceI meganuclease mediates highly efficient transgenesis in fish", Mechanisms of Development, 2002, vol. 118, pp. 91-98.

Luria, A., and Furlow, J. D., "Spatiotemporal retinoid-X receptor activation detected in live vertebrate embryos", Proc Natl Acad Sci USA, 2004, pp. 8987-8992, vol. 101, No. 24.

Voss, S., and Skerra, A., "Mutagenesis of a flexible loop in streptavidin leads to higher affinity for the *Strep*-tag II peptide and improved performance in recombinant protein purification", Protein Engineering, 1997, pp. 975-982, vol. 10, No. 8.

Dooley, K., and Zon, L. I., "Zebrafish: a model system for the study of human disease", Curr Opin Genet Dev, 2000, pp. 252-256, vol. 10.

Zon, L. I., and Peterson, R. T., "In vivo drug discovery in the zebrafish", Nature Reviews Drug Discovery, 2005, pp. 35-44, vol. 4.

Fishman, M. C., "Zebrafish—the canonical vertebrate", Science, 2001, pp. 1290-1291, vol. 294.

Tomita, A., et al., "Recruitment of N-CoR/SMRT-TBLR1 Corepressor Complex by Unliganded Thyroid Hormone Receptor for Gene Repression during Frog Development", Molecular and Cellular Biology, 2004, pp. 3337-3346, vol. 24, No. 8.

Schulman, I.G. and Heyman, R.A., "The Flip Side: Identifying Small Molecule Regulators of Nuclear Receptors", Chemistry & Biology, 2004, pp. 639-646, vol. 11.

Yang, P., et al., "A modified tandem affinity purification strategy identifies cofactors of the *Drosophila* nuclear receptor dHNF4", Proteomics, 2006, pp. 927-935, vol. 6.

* cited by examiner

SEQUENCE LISTING

<160> NUMBER OF SEQ ID NOS: 23

<210> SEQ ID NO 1
<211> LENGTH: 4784
<212> TYPE: DNA
<213> ORGANISM: Artificial sequence
<220> FEATURE:
<223> OTHER INFORMATION: vector

<400> SEQUENCE: 1

```
attaccctgt tatccctact ggagctccac cgcggtcacg taataagtgt gcgttgaatt      60
tattcgcaaa aacattgcat attttcggca aagtaaaatt ttgttgcata ccttatcaaa     120
```

```
aaataagtgc tgcatacttt ttagagaaac caaataatttt tttattgcat acccgttttt    180
aataaaatac attgcatacc ctcttttaat aaaaaatatt gcatactttg acgaaacaaa    240
ttttcgttgc atacccaata aaagattatt atattgcata cccgttttta ataaaataca    300
ttgcataccc tcttttaata aaaatattg catacgttga cgaaacaaat tttcgttgca     360
tacccaataa aagattatta tattgcatac cttttcttgc ataccatttt agccgatcaa    420
ttagatctcc gcggtcaggg gtgtcgcttg gttatttcca aaaatcaaat taattttatt    480
aaactattag aacgagcatg ttttgtctat atgctacaga agataaaaaa taataggagt    540
taacagttat aaaacaacac atttgtttct attgattgtt gaccacactg gggtctcatt    600
aagttagatt aaagacacac taactgggtc aaaagcagca gattgatttc atagcaccag    660
ggtaaacttt ctaacacttt tacggcaatc atatacatta aaattaaata cagaccacga    720
ctgaacaagg aggatgatct ccaatattaa acaaagagac ttgtgcctat ttctctgagg    780
gtaaacatga cctctcaagt tagcaagttg tttttaacac tacaaaaata gttaagacct    840
gcaatcccag aataaagtat tggttttaac caatcaatat agtacagtaa acatccattt    900
gttttgttga aacgttaaac aaatctgacc aaagctatta gcttatataa aacaggtttg    960
ccttctatgt agctgaaaac accacaggcc cgattttgct actgtgtaaa acatttcagc   1020 aagattttt tattgcattt ttttttactg aatcgttcaa acattttatc attttagttt    1080
gttcattcat tgcaactgga aaaacaacac atcacacaac cgcacatatt tcagcaataa   1140
gtacaataaa acactcaaat aaaaaaaaca ttttaaatct ctttgtattt ttgaccgctg   1200
tttcgcgtaa tttcacggta aaactctgga atctccact acattcctct cagcggctcc    1260
tctcaatgac agctgaagaa gtgacggcgg ctgcctgctg tgttttgatt ggtcgaattc    1320
actggaggct tccagaacag tgtagagtct gaacgggtgc gcgctctgct gtatttaaag   1380
ggcgaaagag agaccgcaga gaaactcaac cgaagagaag cgacttgaca agaagaaaa    1440 gagcagcctg acaggacttt tccccgacga ggtgtttatt cgctctattt aagaatctac   1500
tgtaaggtaa gtctcaatat attgtactct attggctaat cagaattata tagagattat   1560
atgtacttaa tgtcaaaaaa tcaactttgt atatgtaatc ttttacatg tggactgcct    1620 atgttcatct tatttaggt ctactagaaa attatatttc ccgttttcac aataaggatt    1680 ttaaaaaag caatgaacag acgggcattt actttatgtt gctgacatta ttttatatga   1740
gcataataac cataaatact agcaaatgtc ctaaatgaat ttgtgttaat gttgtctaca   1800
aaagaaaatt agcgttttac ttgtacaact aataataact tggttattaa gagaatttca   1860
cttgttgact agaaaaatcc tttcataatg aaacaattgc accgataaat tgtataaata   1920
taaaattaat tctaattgtt ttttttttc ctgcaggaat tcgatatcgc ggccgctcta    1980
gagatatcgc caccatggac tacaaagacc atgacggtga ttataaagat catgacatcg   2040
actacaagga tgacgatgac aaggagaacc tgtacttcca gtccaactgg agccacccgc   2100
agttcgaaaa gcatcaccat caccatcacg atatcaagct actgtcttct atcgaacaag   2160
catgcgatat tgccgacttt aaaagctca agtgctccaa agaaaaccg aagtgcgcca    2220 agtgtctgaa gaacaactgg gagtgtcgct actctcccaa aaccaaaagg tctccgctga   2280
ctagggcaca tctgacagaa gtggaatcaa ggctagaaag actggaacag ctatttctac   2340 tgattttcc tcgagaagac cttgacatga ttttgaaaat ggattcttta caggatataa   2400
aagcattgtt aacaggatta tttgtacaag ataatgtgaa taaagatgcc gtcacagata   2460
gattggcttc agtggagact gatatgcctc taacattgag acagcataga ataagtgcga   2520
```

```
catcatcagc tagctgttta aactctagaa ctatagtgag tcgtattacg tagatccaga    2580
catgataaga tacattgatg agtttggaca aaccacaact agaatgcagt gaaaaaaatg    2640
ctttatttgt gaaatttgtg atgctattgc tttatttgta accattataa gctgcaataa    2700
acaagttaac aacaacaatt gcattcattt tatgtttcag gttcagggggg aggtgtggga    2760 ggttttttaa ttcgcggcca tcaagcttat cgataccgtc gacctcgagg ggggcccgg     2820 taccctccaa ggcggagtac tgtcctccgg gctggcggag tactgtcctc cggcaaggtc    2880
ggagtactgt cctccgacac tagaggtcgg agtactgtcc tccgacgcaa ggcggagtac    2940
tgtcctccgg gctgcggagt actgtcctcc ggcaaggtcg gagtactgtc ctccgacact    3000
agaggtcgga gtactgtcct ccgacgcaag gtcggagtac tgtcctccga cactagaggt    3060
cggagtactg tcctccgacg caaggtcgga gtactgtcct ccgacactag aggtcggagt    3120
actgtcctcc gacgcaaggc ggagtactgt cctccgggct ggcggagtac tgtcctccgg    3180
caagggtcga ctctagaggg tatataatgg atcccatcgc gtctcagcct cactttgagc    3240
tcctccacac cggccgctct agaatggtga gcaagggcga ggagctgttc accggggtgg    3300
tgcccatcct ggtcgagctg gacgcgacg taaacgccaa caagttcagc gtgtccggcg     3360
agggcgaggg cgatgccacc tacggcaagc tgaccctgaa gttcatctgc accaccggca    3420
agctgcccgt gccctggccc accctcgtga ccaccctgac ctacggcgtg cagtgcttca    3480
gccgctaccc cgaccacatg aagcagcacg acttcttcaa gtccgccatg cccgaaggct    3540
acgtccagga gcgcaccatc ttcttcaagg acgacggcaa ctacaagacc cgcgccgagg    3600
tgaagttcga gggcgacacc ctggtgaacc gcatcgagct gaagggcatc gacttcaagg    3660
aggacggcaa catcctgggg cacaagctgg agtacaacta caacagccac aacgtctata    3720
tcatggccga caagcagaag aacggcatca aggtgaactt caagatccgc cacaacatcg    3780
aggacggcag cgtgcagctc gccgaccact accagcagaa cacccccatc ggcgacggcc    3840
ccgtgctgct gcccgacaac cactacctga gcacccagtc cgccctgagc aaagacccca    3900
acgagaagcg cgatcacatg gtcctgctgg agttcgtgac cgccgccggg atcactctcg    3960
gcatggacga gctgtacaag agcaggcaca gaaggcatcg ccagcgctct aggagccgca    4020
atcgcagccg aagtcgcagc agtgaacgaa acgccgtca acggagccga agtcgcagca    4080
gtgaacgaag acgctacttg tacaagtaat ctagaactat agtgagtcgt attacgtaga    4140
tccagacatg ataagataca ttgatgagtt tggacaaacc acaactagaa tgcagtgaaa    4200
aaaatgcttt atttgtgaaa tttgtgatgc tattgcttta tttgtaacca ttataagctg    4260
caataaacaa gttaacaaca acaattgcat tcattttatg tttcaggttc aggggggaggt    4320 gtgggaggtt ttttaattcg cggccatcaa gctttcacgt aataagtgtg cgttgaattt    4380
attcgcaaaa acattgcata ttttcggcaa agtaaaattt tgttgcatac cttatcaaaa    4440
aataagtgct gcatactttt tagagaaacc aaataatttt ttattgcata cccgtttttta    4500 ataaaataca ttgcataccc tcttttaata aaaatattg catactttga cgaaacaaat    4560
tttcgttgca tacccaataa aagattatta tattgcatac ccgttttta taaaatacat    4620 tgcataccct cttttaataa aaatattgc atacgttgac gaaacaaatt ttcgttgcat    4680
acccaataaa agattattat attgcatacc ttttcttgcc ataccattta gccgatcaat    4740
tctagtatgg gcccggtacc caattcatta ccctgttatc ccta                    4784
```

<210> SEQ ID NO 2
<211> LENGTH: 43

```
<212> TYPE: DNA
<213> ORGANISM: Artificial sequence
<220> FEATURE:
<223> OTHER INFORMATION: oligonucleotide

<400> SEQUENCE: 2
attcatctag agatatcaag ctactgtctt ctatcgaaca agc          43

<210> SEQ ID NO 3
<211> LENGTH: 50
<212> TYPE: DNA
<213> ORGANISM: Artificial sequence
<220> FEATURE:
<223> OTHER INFORMATION: oligonucleotide

<400> SEQUENCE: 3
attatctaga gtttaaacag ctagctgatg atgtcgcact tattctatgc    50

<210> SEQ ID NO 4
<211> LENGTH: 138
<212> TYPE: DNA
<213> ORGANISM: Artificial sequence
<220> FEATURE:
<223> OTHER INFORMATION: oligonucleotide

<400> SEQUENCE: 4
aattcgacta caaagaccat gacggtgatt ataaagatca tgacatcgac tacaaggatg   60
acgatgacaa ggagaacctg tacttccagt ccaactggag ccacccgcag ttcgaaaagc  120
atcaccatca ccatcacg                                                138

<210> SEQ ID NO 5
<211> LENGTH: 138
<212> TYPE: DNA
<213> ORGANISM: Artificial sequence
<220> FEATURE:
<223> OTHER INFORMATION: oligonucleotide

<400> SEQUENCE: 5
atgatcttta taatcaccgt catggtcttt gtagtcgagt tggactggaa gtacaggttc   60
tccttgtcat cgtcatcctt gtagtcgatg tcaattcgtg atggtgatgg tgatgctttt  120
cgaactgcgg gtggctcc                                                138

<210> SEQ ID NO 6
<211> LENGTH: 40
<212> TYPE: DNA
<213> ORGANISM: Artificial sequence
<220> FEATURE:
<223> OTHER INFORMATION: oligonucleotide

<400> SEQUENCE: 6
attatgatat cgccaccatg gactacaaag accatgacgg              40

<210> SEQ ID NO 7
<211> LENGTH: 30
<212> TYPE: DNA
<213> ORGANISM: Artificial sequence
<220> FEATURE:
<223> OTHER INFORMATION: oligonucleotide

<400> SEQUENCE: 7
attatgatat cgtgatggtg atggtgatgc                        30

<210> SEQ ID NO 8
<211> LENGTH: 48
```

```
<212> TYPE: DNA
<213> ORGANISM: Artificial sequence
<220> FEATURE:
<223> OTHER INFORMATION: oligonucleotide

<400> SEQUENCE: 8
gactcactat agggctaggg ataacagggt aatgaattgg gtaccggg                48

<210> SEQ ID NO 9
<211> LENGTH: 48
<212> TYPE: DNA
<213> ORGANISM: Artificial sequence
<220> FEATURE:
<223> OTHER INFORMATION: oligonucleotide

<400> SEQUENCE: 9
cccggtaccc aattcattac cctgttatcc ctagccctat agtgagtc                48

<210> SEQ ID NO 10
<211> LENGTH: 50
<212> TYPE: DNA
<213> ORGANISM: Artificial sequence
<220> FEATURE:
<223> OTHER INFORMATION: oligonucleotide

<400> SEQUENCE: 10
cggtggagct ccagtaggga taacagggta atcttttgtt ccctttagtg              50

<210> SEQ ID NO 11
<211> LENGTH: 50
<212> TYPE: DNA
<213> ORGANISM: Artificial sequence
<220> FEATURE:
<223> OTHER INFORMATION: oligonucleotide

<400> SEQUENCE: 11
cactaaaggg aacaaaagat taccctgtta tccctactgg agctccaccg              50

<210> SEQ ID NO 12
<211> LENGTH: 28
<212> TYPE: DNA
<213> ORGANISM: Artificial sequence
<220> FEATURE:
<223> OTHER INFORMATION: oligonucleotide

<400> SEQUENCE: 12
attatctaga accatggtga gcaagggc                                      28

<210> SEQ ID NO 13
<211> LENGTH: 28
<212> TYPE: DNA
<213> ORGANISM: Artificial sequence
<220> FEATURE:
<223> OTHER INFORMATION: oligonucleotide

<400> SEQUENCE: 13
attatctaga ttacttgtac aagtagcg                                      28

<210> SEQ ID NO 14
<211> LENGTH: 38
<212> TYPE: DNA
<213> ORGANISM: Artificial sequence
<220> FEATURE:
<223> OTHER INFORMATION: oligonucleotide

<400> SEQUENCE: 14
attatccgcg gggtaccctc caaggcggag tactgtcc                           38
```

<210> SEQ ID NO 15
<211> LENGTH: 35
<212> TYPE: DNA
<213> ORGANISM: Artificial sequence
<220> FEATURE:
<223> OTHER INFORMATION: oligonucleotide

<400> SEQUENCE: 15
ataatcggcc ggtgtggagg agctcaaagt gaggc                              35

<210> SEQ ID NO 16
<211> LENGTH: 28
<212> TYPE: DNA
<213> ORGANISM: Artificial sequence
<220> FEATURE:
<223> OTHER INFORMATION: oligonucleotide

<400> SEQUENCE: 16
attatccgcg gtcaggggtg tcgcttgg                                      28

<210> SEQ ID NO 17
<211> LENGTH: 32
<212> TYPE: DNA
<213> ORGANISM: Artificial sequence
<220> FEATURE:
<223> OTHER INFORMATION: oligonucleotide

<400> SEQUENCE: 17
attatgcggc cgcgatatcg aattcctgca gg                                 32

<210> SEQ ID NO 18
<211> LENGTH: 28
<212> TYPE: DNA
<213> ORGANISM: Artificial sequence
<220> FEATURE:
<223> OTHER INFORMATION: oligonucleotide

<400> SEQUENCE: 18
ataaccgcgg tcacgtaata agtgtgcg                                      28

<210> SEQ ID NO 19
<211> LENGTH: 34
<212> TYPE: DNA
<213> ORGANISM: Artificial sequence
<220> FEATURE:
<223> OTHER INFORMATION: oligonucleotide

<400> SEQUENCE: 19
ataaccgcgg agatctatac tagaattgat cggc                               34

<210> SEQ ID NO 20
<211> LENGTH: 28
<212> TYPE: DNA
<213> ORGANISM: Artificial sequence
<220> FEATURE:
<223> OTHER INFORMATION: oligonucleotide

<400> SEQUENCE: 20
ataaaagctt tcacgtaata agtgtgcg                                      28

<210> SEQ ID NO 21
<211> LENGTH: 28
<212> TYPE: DNA
<213> ORGANISM: Artificial sequence
<220> FEATURE:
<223> OTHER INFORMATION: oligonucleotide

<400> SEQUENCE: 21
ataagggccc atactagaat tgatcggc				28

<210> SEQ ID NO 22
<211> LENGTH: 178
<212> TYPE: PRT
<213> ORGANISM: Artificial sequence
<220> FEATURE:
<223> OTHER INFORMATION: polypeptide

<400> SEQUENCE: 22

Met Asp Tyr Lys Asp His Asp Gly Asp Tyr Lys Asp His Asp Ile Asp
1               5                   10                  15

Tyr Lys Asp Asp Asp Asp Lys Glu Asn Leu Tyr Phe Gln Ser Asn Trp
                20                  25                  30

Ser His Pro Gln Phe Glu Lys His His His His His Asp Ile Lys
            35                  40                  45

Leu Leu Ser Ser Ile Glu Gln Ala Cys Asp Ile Cys Arg Leu Lys Lys
    50                  55                  60

Leu Lys Cys Ser Lys Glu Lys Pro Lys Cys Ala Lys Cys Leu Lys Asn
65                  70                  75                  80

Asn Trp Glu Cys Arg Tyr Ser Pro Lys Thr Lys Arg Ser Pro Leu Thr
                85                  90                  95

Arg Ala His Leu Thr Glu Val Glu Ser Arg Leu Glu Arg Leu Glu Gln
            100                 105                 110

Leu Phe Leu Leu Ile Phe Pro Arg Glu Asp Leu Asp Met Ile Leu Lys
        115                 120                 125

Met Asp Ser Leu Gln Asp Ile Lys Ala Leu Leu Thr Gly Leu Phe Val
130                 135                 140

Gln Asp Asn Val Asn Lys Asp Ala Val Thr Asp Arg Leu Ala Ser Val
145                 150                 155                 160

Glu Thr Asp Met Pro Leu Thr Leu Arg Gln His Arg Ile Ser Ala Thr
                165                 170                 175

Ser Ser

<210> SEQ ID NO 23
<211> LENGTH: 281
<212> TYPE: PRT
<213> ORGANISM: Aequorea victoria

<400> SEQUENCE: 23

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly

-continued

```
            115                 120                 125
Ile Asp Phe Lys Glu Asp Gly Asn Ile Leu Gly His Lys Leu Glu Tyr
        130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys Ser
225                 230                 235                 240
Arg His Arg Arg His Arg Gln Arg Ser Arg Ser Arg Asn Arg Ser Arg
                245                 250                 255
Ser Arg Ser Ser Glu Arg Lys Arg Arg Gln Arg Ser Arg Ser Arg Ser
            260                 265                 270
Ser Glu Arg Arg Arg Tyr Leu Tyr Lys
        275                 280
```

METHODS AND COMPOSITIONS FOR THE DETECTION AND ISOLATION OF LIGANDS

FIELD OF THE INVENTION

The invention relates to methods and compositions for the detection and isolation of ligands. In particular, the invention relates to detection and isolation of ligands in live animals.

BACKGROUND OF THE INVENTION

The activities of many regulatory proteins and RNAs can be modulated by small molecule ligands that move freely within and between living cells. The mobility of these small molecules, and their effects on important cellular targets, make them excellent candidates for pharmaceutical development. Indeed, the National Institute of Health has declared a need to find small molecule ligands for every protein encoded in the genome. The discovery of therapeutic small molecules and their targets is also the primary focus of most pharmaceutical companies. The Nuclear Receptor ("NR") superfamily of transcription factors comprises a particularly attractive set of small molecule targets. Unlike most other transcription factors, NRs are normally switched on and off by small lipids or lipophilic molecules. Furthermore, NRs feature in practically every fundamental biological process, functioning as key control points in key signaling and metabolic pathways {Mangelsdorf, 1995; Chawla, 2001}. The pivotal roles played by these proteins, and their potential for functional manipulation by natural and synthetic ligands, make them ideal targets for medical study and drug intervention.

The human genome contains 48 members of the NR superfamily. These proteins share a common structural organization, including a central, zinc finger DNA-binding domain ("DBD"), and C-terminal to this, a structurally conserved ligand-binding domain ("LBD") {Kumar, 1999}. In addition to forming the ligand-binding pocket, the LBD is also involved in homo- and/or hetero-dimerization and possesses ligand-regulated binding sites for transcriptional co-activators and co-repressors {Egea, 2000; Wagner, 1995; Renaud, 1995; Uppenberg, 1998; Bledsoe, 2002; Dhe-Paganon, 2002; Gampe, 2000}. Most LBDs characterized to date are composed of approximately 12 α-helices arranged in three layers to form a hydrophobic ligand-binding pocket in the centre. Examples of NR ligands include steroid hormones, thyroid hormones, bile acids, fatty acids, certain vitamins and prostaglandins {Francis, 2003; Bogan, 1998}. Ligand binding induces structural changes in the LBD, such that, in the case of activators, the position of helix 12 is altered resulting in the displacement of co-repressors, recruitment of coactivators and subsequent target gene transcription {Glass, 2000}. Ligands whose binding promotes the transcriptional activation of target genes, termed agonists, induce different structural changes in LBDs than antagonists. Antagonists tend to possess bulky chemical groups that cannot be properly accommodated in the binding pocket, preventing the proper placement of helix 12 for coactivator binding {Glass, 2000}.

NRs play major roles in most physiological processes. These include sex determination {McElreavey, 1999}, maturation {Beuschlein, 2002}, growth control {Zhao, 2001}, metabolism {Basu-Modak, 1999}, neuronal growth and differentiation {Zhou, 1999; Satoh, 2002}, neuroendocrine function {Auger, 2000; Tetel, 2000} electrolyte homeostasis {Turnamian, 1990}, immune responses, xenobiotic responses {Kliewer, 1999; Kliewer, 2002; Willson, 2002}, circadian rhythm and aging {Pardee, 2004}. When NRs malfunction, major diseases ensue, some of which are listed below. By understanding NR functions and the ligands that control them, there is the potential to control the many diseases associated with inappropriate NR activity. There are already many very successful examples of this. One of the more familiar is the control of Estrogen Receptor (ER) activity in breast tumours by the synthetic antagonists tamoxifen and raloxifene {Tonetti, 1999; Osborne, 2000}. RXR- and RAR-directed retinoid analogs have proven successful in the treatment of acute promyelocytic leukemias {Degos, 1995} and glaucoma {Kim, 1990; Stoilov, 2001}. A great deal of attention has also been focused on the development of ligands for LXRs, PPARs and HNF4, which play major roles in hyperlipidaemia, atherosclerosis, diabetes and obesity {Kersten, 2000; Repa, 2002; Willson, 2001; Way, 2001; Wakino, 2002; Bogan, 2000}. Until recently, each of these NRs were orphans whose ligand(s) were unknown. Some of the most recent orphan NRs to gather attention are FXR, PXR and CAR, which all play major roles in xenobiotic responses {Stoilov, 2001; Willson, 2002; Xie, 2000; Kliewer, 1999; Kliewer, 2002; Kliewer, 2002}. Modulating the activities of these receptors can decrease occurrences of drug resistance and drug-drug incompatibility, which are major problems in drug treatment plans. Other major diseases known to be caused by inappropriate NR activity include Parkinson's disease {Satoh, 2002; Lee, 2002; Rawal, 2002}, cardiac myopathies {Zhu, 2003; Huss, 2002} and asthma {Bolt, 2001; Serhan, 2001}.

The potential of future NR-directed pharmaceuticals to control normal and abnormal biological processes is reflected by the percentage of top-selling drugs present on the market (>10%). This large presence is despite the fact that relatively few NRs have been successfully targeted. The large subfamily of orphan NRs yet to be targeted has the potential to define critical new biological processes and physiological pathways. Hence, they also represent an untapped resource for drug discovery and disease treatment. Even with the NRs that have known ligands, more potent, selective, stage- and tissue-specific agonists/antagonists need to be identified and developed. Further fine-tuning of drug specificities is also required to alleviate the cross-reactivity, cross talk and unwanted side effects of existing ligands. For example, tamoxifen, which is used to inactivate the Estrogen receptor (ER) in breast tumours, also blocks normal and necessary functions of the receptor in other tissues. Tamoxifen also cross-reacts with other NR. It is likely that new ER agonists and antagonists can be developed that act stage- and tissue-specifically and far more selectively.

The first NR ligands identified were hormones such as the insect metamorphosis-inducing steroid ecdysone and the female-specific steroid estrogen. The powerful effects of these hormones allowed for the large-scale and complex purification schemes necessary for their ultimate identification. However, the complexity of these purification procedures, the lack of suitable assays and the unsuitable biochemical nature of most ligands make conventional purification methods tedious, unsuitable or impossible for the remaining NR ligands.

Methods currently used to identify NR ligands involve in vitro based or cultured cell based screens. Most in vitro screening methods depend on ligand-mediated enhancement of coactivator peptide binding. One example of this is the ALPHAScreen, which makes use of time-resolved fluorescence resonance energy transfer (FRET) {Glickman, 2002}. The major drawback of all in vitro approaches, however, is that conditions and cofactors required for LBD stability and ligand and/or coactivator binding are likely to be missing. This means that many compounds with potential activity may be passed over. Also, compounds that do prove to be active in the test tube may prove unsuitable in vivo. For example, they may be unable to penetrate cells or tissues, they may be rapidly modified or degraded, or they prove to be toxic due to numerous off-target effects.

In the case of cultured cells, the most widely used screening methods involve ligand-stimulated reporter gene activation {Dias, 1998; Grover, 2003}. FRET has also been used to detect ligand-mediated LBD-cofactor interactions {Llopis, 2000; Day, 1998; Weatherman, 2002}. A yeast-based approach, that detects ligand mediated refolding of LBDs that are fused to yellow fluorescent protein (YFP), has also recently been developed {Muddana, 2003}. As with in vitro approaches, however, each of these cell-based assays is limited by the presence or absence of appropriate and inappropriate cofactors and conditions restricted to the particular cell type chosen for the assay. For example, alternative cofactors bound by a given NR in one cell type are often absent in others. In addition, the binding, delivery and function of some ligands only works in certain cell types. Also, as with the in vitro based assays, these compounds may prove to be unstable or toxic in a whole-animal system. Indeed, the majority of compound hits fail when subsequently tested in live model organisms. Thus in vitro and cultured cell based results, while high in throughput, tend not to be predictive of in vivo utility.

Further evidence that ligands with tissue-specific efficacy exist and are important is the observation that different ligands for tissue-specific receptors promote distinct changes in LBD conformations. These alternative conformations are likely to have different outcomes in different cell types due to the diversity of cofactors and cofactor modifications capable of interacting with these alternative conformations. Thus, a full understanding of in vivo NR function requires elucidation of the ligands that are active in each tissue of the living animal. Ultimately, this requires the testing of compounds in the entire organism during all stages of development, as well as adulthood and senescence.

SUMMARY OF THE INVENTION

The present inventors provide a "ligand-trap" assay that uses a novel composition to create transgenic animals that allow for in vivo detection of ligand binding and subsequent purification and identification of the bound ligand(s).

Accordingly, the present invention provides a composition comprising
(a) a first nucleic acid encoding a fusion protein of a DNA-binding domain, a ligand-binding domain and multiple different affinity tags; and
(b) a second nucleic acid comprising a promoter having binding sites for the DNA-binding domain and encoding a reporter protein.

In another embodiment, the first and second nucleic acids are on a single vector.

The invention further provides an in vivo method for detecting an endogenous ligand comprising
(a) providing an animal having the first and second nucleic acids of the composition of the invention either transiently expressed or incorporated into its genome;
(b) inducing expression of the first nucleic acid; and
(c) detecting a change, if any, in expression of the reporter protein, wherein the change indicates that at least one endogenous ligand is present.

In another embodiment, the invention provides an in vivo method for screening a test compound for its ability to interact with a ligand-binding domain comprising (a) providing an animal having the first and second nucleic acids of the composition of the invention either transiently expressed or incorporated into its genome;
(b) contacting the transgenic animal with the test compound or condition;
(b) inducing expression of the first nucleic acid; and
(c) detecting a change, if any, in expression of the reporter protein, wherein the change indicates that the test compound or condition affects the activity of the ligand-binding domain (directly or indirectly).

The invention further provides a method for purifying the fusion protein, along with bound ligand(s) or test compound(s) that bind to the protein encoded by the first nucleic acid. Accordingly, the invention provides a method for purifying modulators of the reporter system that act via direct molecular interactions, the method comprising
(a) providing an animal having the first and second nucleic acids of the composition of the invention either transiently expressed or incorporated into its genome;
(b) inducing expression of the first nucleic acid;
(c) detecting a signal;
(d) generating a cellular extract from the responding animal or tissues; and
(e) subjecting the cellular extract generated in step (d) to multiple affinity purification steps, each step comprising binding one affinity tag to an affinity resin capable of selectively binding the one affinity tag and eluting the affinity tag from the affinity resin after substances not bound to the fusion protein have been removed.

In another embodiment, the invention provides a method for purifying a modulator of a reporter system, the method comprising
(a) providing an animal having the first and second nucleic acids of the composition of the invention either transiently expressed or incorporated into its genome;
(b) contacting the transgenic animal with a test compound;
(c) inducing expression of the first nucleic acid;
(d) detecting a signal;
(e) generating a cellular extract from the responding animal or tissues; and
(f) subjecting the cellular extract generated in step (e) to multiple affinity purification steps, each step comprising binding one affinity tag to an affinity resin capable of selectively binding the one affinity tag and eluting the affinity tag from the affinity resin after substances not bound to the fusion protein have been removed.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

The present inventors have developed a high throughput approach for the identification and functional testing of ligands, preferably nuclear receptor (NR) protein ligands in vivo. The technology makes use of a multifunctional reporter system to signal the presence of ligands in live animals, and to isolate and identify those ligands and cofactors that are directly bound to activated receptors.

Figure 1:
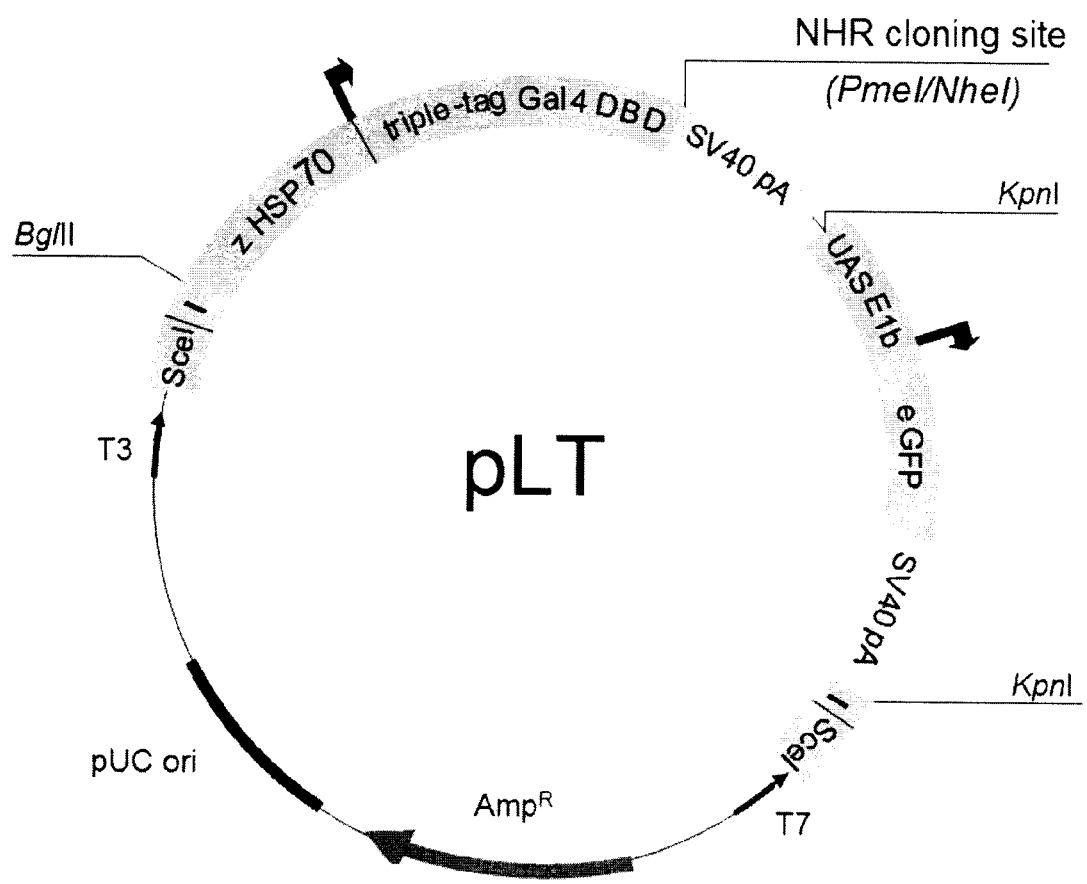
FIG. 1 shows the bifunctional ligand trap vector (pLT) used to verify the functionality of the invention, referred to as "ligand trapping". The pLT vector encodes a triple-tagged GAL4 DNA-binding domain, under the control of an inducible heat shock promoter and followed by restriction sites for adding in-frame ligand-binding domains. The resulting fusion proteins serve as ligand-regulated transcription factors that can be affinity purified to identify bound ligands. The pLT vector also contains a GFP ligand detection reporter system comprised of multiple GAL4 binding sites upstream of a basal promoter and a GFP reporter gene. Binding of a transcriptionally active GAL4-ligand-binding domain fusion protein to these GAL4 binding sites results in GFP expression. Amp=Ampicillin resistance; T7; T3=T7 or T3 polymerase promoter; zHSP70=zebrafish hsp70 gene promoter; triple tag=3× Flag tag, Tev cleavage site, Strep II tag, and 6×His tag. Gal4 DBD=Gal 4 DNA-binding domain, amino acids 1-132. NR=nuclear hormone receptor. SV40 pA=SV 40 polyadenylation signal. UAS=upstream activating sequence. E1b=adenoviral basal promoter. eGFP=enhanced green fluorescent protein.
Figure 2:
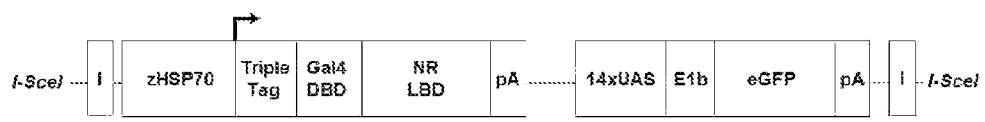
FIG. 2 describes the function of the ligand detection portion of the ligand trap system. (a) Composition of the ligand-detecting fusion protein. The DNA-binding domain (DBD) of GAL4 is fused N-terminal to a triple-tag and C-terminal to a NR LBD under the control of a heat shock promoter (hsp). (b) Fusion protein transcriptional activity is monitored with a $GAL4_{UAS}$-regulated GFP reporter. When the GAL4 DBD fusion protein binds to the reporter, and ligands and coactivators are present, GFP is expressed. (c) Example of a ligand sensor system response in a Danio rerio (zebrafish) embryo. Sites of GFP fluorescence (white nuclear dots) correspond to cells that contain endogenous activating ligand(s).
Figure 2:
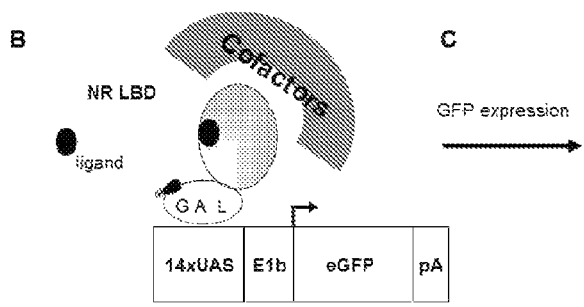
Figure 2:
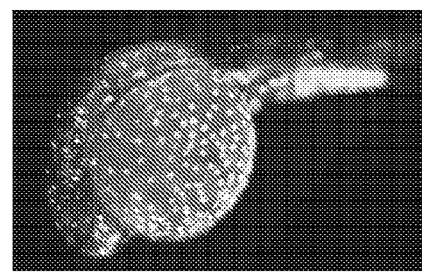
Figure 3:
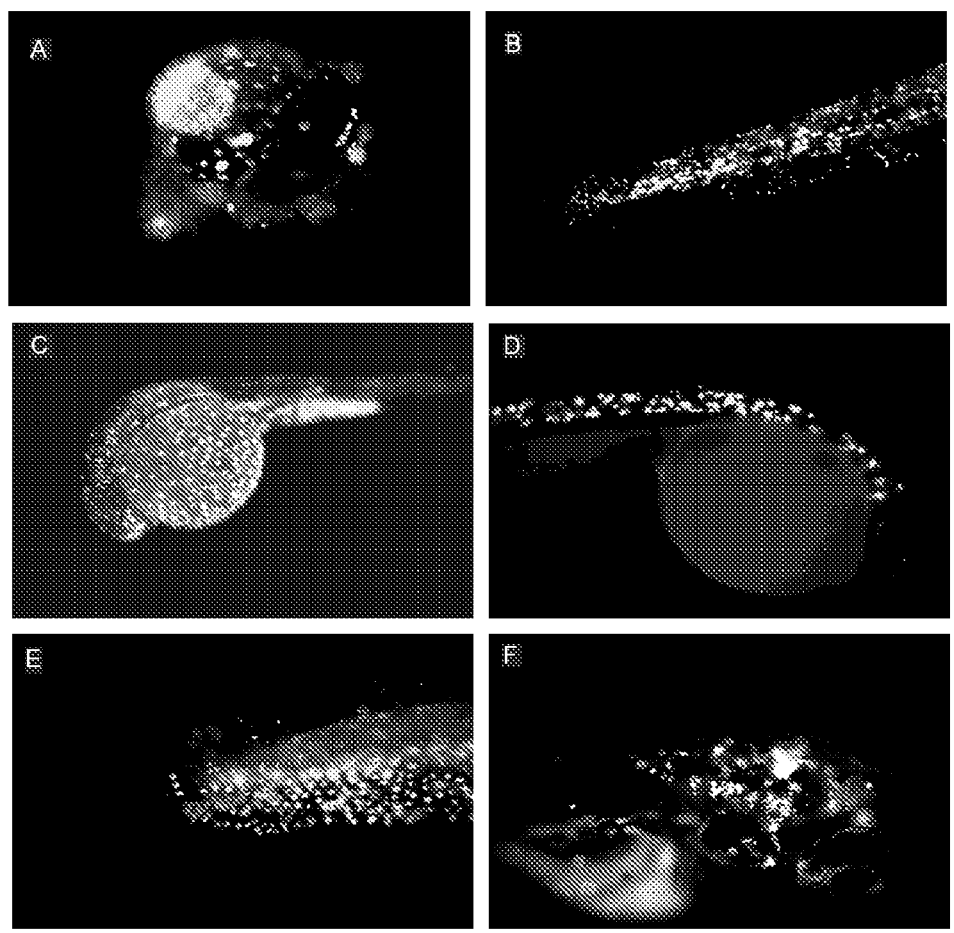
FIG. 3 shows that different NR ligand trap constructs exhibit unique patterns of activity in developing embryos: GFP expression was monitored after 24 hpf, 48 hpf or 72 hpf. No GFP signal is detected when the GAL4 DNA-binding domain is not fused to a ligand-binding domain (LBD). A, B) F0 fish injected with different ligand trap NRs showing transient GFP expression. C—H) Transgenic F1 ligand-trap embryos. Receptor activity is observed in the yolk, midbrain and forehead of Rev-ErbAα fish (A), the yolk, heart, central nervous system (CNS), eyes and adipose tissue of TRα fish (B, C), the spine of PPAR γ fish (D), the brain of RAR β fish (E) and the brain and CNS of LXRα fish (F).

In particular, the inventors have tested and validated a novel "ligand trap" system. The primary components of this system are an NR ligand-binding domain (LBD) fused to the DNA-binding domain of GAL4, a GAL4 promoter-regulated GFP reporter gene and a StrepII/His/FLAG triple-affinity tag fused to the GAL4-LBD fusion protein (FIGS. 1, 2). In the animal, the localized binding (or disassociation) of ligands converts the GAL4-LBD fusion protein into a transcriptional activator that binds and activates the reporter gene promoter, leading to local GFP expression (FIG. 2).

Compositions of the Invention

The present invention provides a composition having a first nucleic acid that encodes a chimeric transcription factor that has DNA-binding, ligand-binding and affinity tag portions and a second nucleic acid that encodes a reporter component that is capable of detecting the consequences of ligand association with the chimeric transcription factor.

Accordingly, in one embodiment, the present invention provides a composition comprising
  (a) a first nucleic acid encoding a fusion protein of a DNA-binding domain, a ligand-binding domain and multiple different affinity tags; and
  (b) a second nucleic acid comprising a promoter having binding sites for the DNA-binding domain and encoding a reporter protein.

The term "DNA-binding domain" as used herein means a protein domain that is capable of binding a promoter sequence. DNA-binding domains not likely to recognize heterologous host DNA sequences are known in the art, such as those of GAL4, LexA, and Lambda repressor. In a preferred embodiment, the DNA-binding domain is from a non-vertebrate transcription factor that has limited capacity to bind host DNA sequences (to prevent interference with host gene genome function). In a particular embodiment, the DNA-binding domain is from the yeast transcription factor Gal4.

The term "ligand-binding domain", as used herein, means a sequence that is able to interact with another molecule, including proteins, nucleic acids, small molecules or post-translational modifications. A person skilled in the art could use any ligand-binding domain of interest. The composition of the invention is particularly useful for co-purifying (trapping) ligands that are normally difficult to isolate. For example, the ligand-binding domain of a nuclear receptor may be used. Table 1 provides a list of human NR receptors tested thus far. Accordingly, in a particular embodiment, the ligand-binding domain is derived from a nuclear receptor.

Although focused on NR, the methods and compositions described here can be adapted to many other types of proteins or RNAs. For example, kinases, dehydrogenases, acyl transferases, and PAS domain proteins are small molecule binding proteins that could work equally well. As a more complex example of the invention, one could co-express a Gal4 DNA-binding domain fusion protein containing the MS2 coat protein, along with an RNA sequence comprising an MS2 coat protein binding motif fused to an RNA bait sequence, to discover VP16-coupled RNA binding proteins that bind the bait RNA sequence.

The term "ligand" as used herein can be any molecule that is capable of binding to the ligand-binding domain of the fusion protein. Examples include natural products such as peptides, proteins, nucleic acids, lipids, sugars, metals, as well as assorted synthetic compounds.

Figure 4:
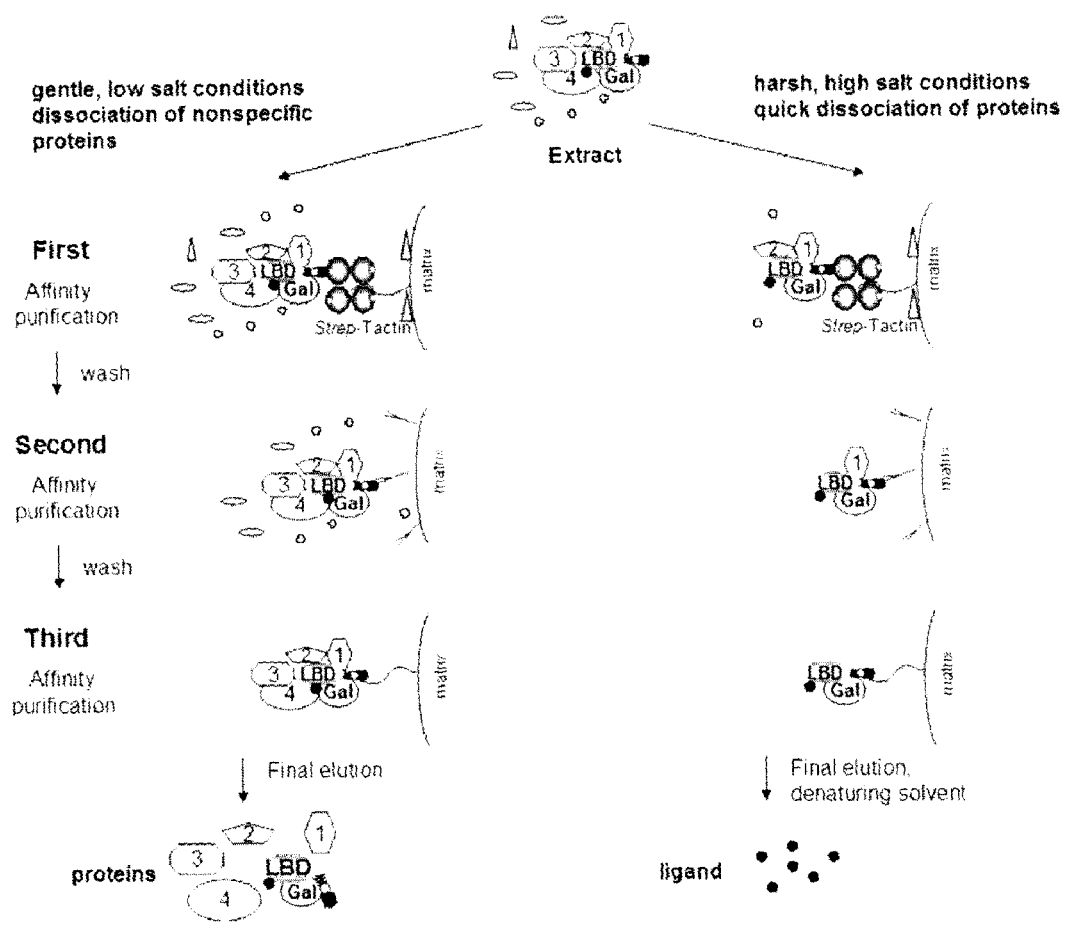
FIG. 4 shows a schematic illustration of the triple-tag (3×FLAG-Strep II-6×His) affinity purification procedure: The ligand trap bait construct (triple tag-Gal4 DBD-NR LBD) is expressed in cells or animals and is purified using triple affinity purification. The purification can either be performed under gentle (ie: low salt for protein cofactors) or harsh (ie: high salt for lipophilic ligands) conditions. Eluted ligands can be identified by MALD-TOV or ESI mass spectrometry (proteins, peptides), or by non-denaturing, ESI or gas-coupled mass spectrometry (small molecules).

The choice of a highly efficient set of affinity tags, such as those used herein, provides the levels of fusion protein purification (up to $10^9$-fold with 70% yield) required to copurify enough ligand from complex cells or tissues to permit identification by mass spectrometry (procedure diagramed in FIG. 4). Besides identifying novel ligands, this approach provides confirmation that agonists or antagonists exert their effects via direct interactions with the ligand-binding domain. For this purpose, the tags must be motifs, fused to the bait fusion protein (DNA-binding domain fused to ligand-binding domain), that bind strongly and specifically to a substrate that can be covalently coupled to a resin. Furthermore, the tag-substrate interaction must be readily dissociated by conditions that do not disrupt interactions between the bait and specifically-interacting molecules.

In one embodiment, the first nucleic acid encodes at least two different affinity tags. In another embodiment, the first nucleic acid encodes at least three different affinity tags, each with an ability to provide approximately 1000-fold purification or higher with yields of 50% or higher. This would yield sufficient levels of bait and ligands/cofactors from animal tissues for identification by mass spectrometry.

In a preferred embodiment, the multiple different affinity tags are the triple-tag comprising StrepII/His/FLAG. The 3×FLAG used binds to an anti-FLAG monoclonal antibody and is released by adding excess FLAG peptide, or optionally, in the case of the triple-tag used here, by TEV protease cleavage of the tag from the bait protein. The StrepII tag binds to streptavidin and is efficiently dissociated from streptavidin by desthiobiotin or biotin. The 6×His tag binds to metals such as $Cu^{++}$ and can be released using imidazole. Each of these tags fulfills the requirements described above. Furthermore, they work in low salt, high salt or denaturing conditions, allowing the selective purification of ionically associated, hydrophobically associated or covalently bound molecules, respectively.

In another embodiment, the first nucleic acid further comprises an inducible promoter to avoid any deleterious effects caused by expression of the encoded fusion protein. The term "inducible promoter" as used herein means a promoter sequence that allows transcription only in the presence of the inducible element. A person skilled in the art could readily choose an appropriate inducible promoter that would not interfere with development or function in vivo. For example, a heat- or cold-inducible promoter may be used wherein transcription only occurs upon a shift in temperature. Accordingly, in one embodiment the inducible promoter is heat, transcription factor, or hormone activated. In the preferred embodiment, GAL4 and hormones are already used/involved, making them inappropriate for use. Hence, a heat-inducible hsp70 promoter is used to control transcription of the chimeric transcription factor.

The term "reporter protein" as used herein means any protein that when expressed is detectable in live cells or animals. Such currently available reporter proteins include green fluorescent proteins, red fluorescent proteins, DS-red and luciferase. In one embodiment, the reporter protein is enhanced green fluorescent protein (eGFP).

In one embodiment, the first and second nucleic acids are on different vectors. In another embodiment, the first and second nucleic acids are on a single vector. In a particular embodiment, the single vector comprises the nucleotide sequence as shown in SEQ ID NO:1 (Table 2).

Methods and Uses of the Present Invention

One use of the compositions of the invention is for in vivo ligand detection. In one embodiment, the first and second nucleic acids are used to create two transgenic animals, each expressing one of the nucleic acids. The transgenic animals are then genetically crossed in order to signal the presence of activated LBD fusion proteins. In another embodiment, the first and second nucleic acids are on a single vector used to create a transgenic animal that is capable of expressing both the fusion protein and reporter protein. The compositions of the invention can also be used transiently within cultured cells or non-transgenic animals.

Although it has previously been shown that GAL4 LBD fusions could be used to detect the presence of ligands in cultured cells or fixed tissues these fusions and detection systems were unsuitable for the screening of candidate ligand compounds. Activities could not be monitored unless the animals were sacrificed and the appropriate tissues dissected, sectioned and fixed. These methods only provide restricted snapshots of the tissues and stages selected. They are also extremely labor-intensive, making them unsuitable for screening. Furthermore, compounds could not be applied to these previously used transgenic animals unless fed or injected. By combining the use of fluorescent protein reporters (i.e. GFP, RFP, DS-red etc.), and co-expressing LBDs fused to an appropriate DNA binding motif (i.e. GAL4, LexA Nuclear receptor etc), the present inventors have been able to detect the presence of endogenous or exogenously added ligands in live animals, in most tissue types and at all stages of development (eg FIG. 5, 7, Table 1 and {Palanker, 2006}).

Accordingly, the present invention provides a method of detecting an endogenous ligand in vivo comprising (a) providing an animal having the first and second nucleic acids of the composition of the invention either transiently expressed or incorporated into its genome;

(b) inducing expression of the first nucleic acid; and (c) detecting a change, if any, in expression of the reporter protein, wherein the change indicates that at least one endogenous ligand is present.

The term "endogenous ligand" as used herein means any molecule that exists in vivo that is capable of interacting with the ligand-binding domain. Such ligands potentially include polypeptides, nucleic acids, lipids, sugars, metal ions, other naturally occurring molecules, post-translational modifications or ingested xenobiotics and pollutants.

The present invention also allows screening of a test compound for its ability to interact with the ligand-binding domain. This provides the ability to screen for new modulators of the target protein. This system also determines whether the added modulators act tissue or stage-specifically, whether they act positively or negatively and what concentration levels are effective. Importantly, it also selects for modulators that are stable, non-toxic and specific. The latter are problems that eliminate the use of 9,999 of every 10,000 modulators identified via in vitro or tissue-culture based assays when followed up with in vivo testing and clinical trials. Accordingly, in another embodiment, the present invention provides an in vivo method for screening exogenously provided test compounds for their ability to interact with or otherwise regulate a ligand-binding domain, said method comprising
  (a) providing an animal having the first and second nucleic acids of the composition of the invention either transiently expressed or incorporated into its genome;
  (b) contacting the animal with the test compound;
  (c) inducing expression of the first nucleic acid; and
  (d) detecting a change, if any, in expression of the reporter protein, wherein the change indicates that the test compound interacts, directly or indirectly, with the ligand-binding domain.

The term "test compound" as used herein means any exogenous compound that is added, applied, introduced or induced in the animal. Examples include, but are not limited to, any of the ligand types listed above.

The term "transgenic animal" as used herein means an animal that has been made by the addition of exogenous nucleic acid sequences incorporated into its genome. In the present invention, the first and second nucleic acids of the composition of the invention are used to create a transgenic animal. In one embodiment, a first transgenic animal is created using the first nucleic acid of the composition and a second transgenic animal is created using the second nucleic acid of the composition and then the first and second transgenic animals are crossed to produce a transgenic animal that has the first and second nucleic acid incorporated into its genome. Transgenic animals can be made using random integration, homologous recombination, transposable element integration or recombinase assisted integration {Kawakami, 2000; Davidson, 2003}. In one embodiment, the enzyme I-SceI is used to introduce the first and second nucleic acids of the composition into the host genome {Thermes, 2002}. I-SceI provides the advantages of efficient integration, low copy number integration, and large insert size.

Finally, transgenic animals can be generated that carry all components in one vector making genetic crosses unnecessary, and ligand detection and biochemical characterization performed using a single transgenic line. Accordingly, in another embodiment, a single transgenic animal is created using a single vector that contains the first and second nucleic acid of the composition.

The methods of the invention can be used in any transgenic animal. In one embodiment, the transgenic animal is selected from the group consisting of *C. elegans, Drosophila, Xenopus*, mouse or zebrafish.

The term "transiently expressed" as used herein means that the first and/or second nucleic acid(s) have not been incorporated into the host genome or germline.

The zebrafish has many key advantages that make it the model organism of choice for the compositions and methods described. Zebrafish develop rapidly, are inexpensive to grow, and thousands of eggs/embryos are easily collected and small enough to be aliquoted into multi-well plates where minute amounts of test compounds can be used (i.e. 10 µM in 100 µl per well). Importantly, the eggs, embryos, and adults absorb chemicals directly from water and are DMSO tolerant. Moreover, the embryos are transparent, which makes them ideal for GFP analysis in live animals. Zebrafish also share very high sequence conservation with human genes. In the case of NR, all human NRs have orthologues in zebrafish, and comparison of their LBDs reveals average identities of about 75% {Maglich, 2003}. Cofactor recruitment and ligand recognition between fish and human NR LBDs is highly conserved. The fish glucocorticoid receptor (GR), for example, is able to induce transcriptional activity in the presence of cortisol and dexamethasone, and shows inhibition of transactivation with the human GR antagonist RU486 {Bury, 2003}. Fish estrogen receptors (ERα and β) have also been shown to have high binding affinities for diverse natural and synthetic human ER ligands {Kloas, 2000; Hawkins, 2000}.

Accordingly, in a particular embodiment, the transgenic animal is zebrafish.

Figure 5:
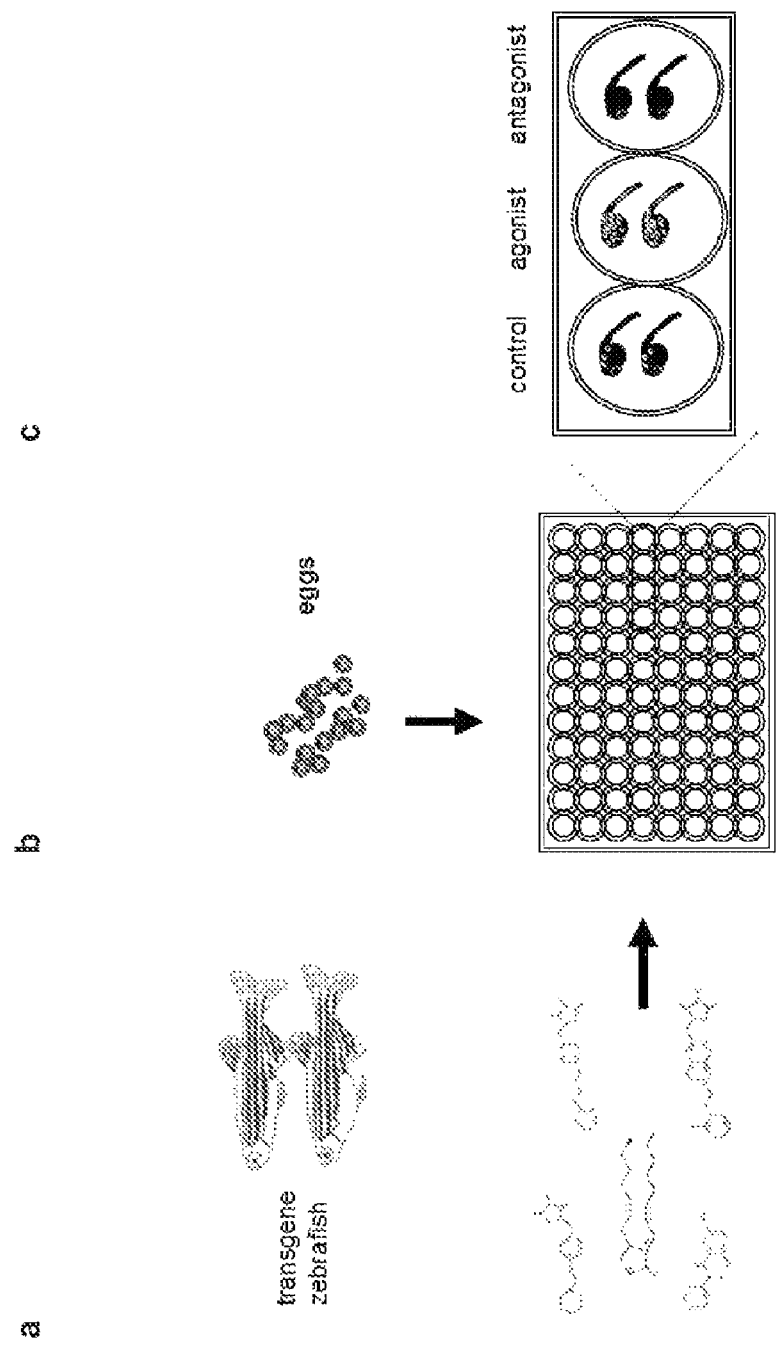
FIG. 5 depicts the screening method for exogenous ligands: (a) Transgenic ligand trap fish are mated, producing 200-300 eggs per female. Eggs/embryos/fish are distributed to multi-well assay plates after heat shock, with 3-6 specimens per well. (b) A small-molecule library or an extract that contains potential ligands is added to each well. (c) After a period of incubation, reporter (GFP) expression is monitored and compared to controls. Agonists induce novel GFP expression, or broaden and strengthen endogenous responses. Antagonists suppress GFP expression induced by endogenous agonists. Referral to the library database reveals the identities of new nuclear receptor agonists or antagonists.

The multi-tag system fused to the chimeric transcription factor provides a powerful and efficient purification system capable of yielding sufficient levels of purified LBD protein for the identification of specifically associated molecules (FIG. 5). This provides a new and powerful means to identify endogenous ligands, and to determine whether exogenously provided modulators work directly or indirectly. The identification of endogenous and exogenous nuclear receptor ligands in/from live animals, via purification of the cognate receptor, has never before been suggested or attempted. This is due primarily to the enormous purification factors required to isolate sufficient levels of pure protein from complex tissues. In addition, techniques available for the isolation and identification of small quantities of extracted ligand were unavailable. The present tagging system, coupled with optimized methods of ligand extraction and identification via new and improved mass spectrometry techniques, now makes this approach feasible. Accordingly, in another embodiment, the invention provides a method for purifying a ligand of a reporter system, the method comprising:
  (a) providing an animal having the first and second nucleic acids of the composition of the invention either transiently expressed or incorporated into its genome;
  (b) inducing expression of the first nucleic acid;
  (c) detecting a signal;
  (d) generating a cellular extract from the animal; and
  (e) subjecting the cellular extract generated in step (d) to multiple affinity purification steps, each step comprising binding one affinity tag to an affinity resin capable of selectively binding one affinity tag and eluting the affinity tag from the affinity resin after substances not interacting with the fusion protein have been removed.

In another embodiment, the method further comprises subjecting the purified material of step (e) to appropriate, high-sensitivity analytical techniques such as MALDI-TOV, ESI, GC or semi non-denaturing mass spectrometry.

Accordingly, in another embodiment, the invention provides a method for purifying a ligand of a reporter system, the method comprising:

(a) providing an animal having the first and second nucleic acids of the composition of the invention either transiently expressed or incorporated into its genome;
(b) contacting the transgenic animal with a test compound;
(c) inducing expression of the first nucleic acid;
(d) detecting a signal;
(e) generating a cellular extract from the transgenic animal; and
(f) subjecting the cellular extract generated in step (e) to multiple affinity purification steps, each step comprising binding one affinity tag to an affinity resin capable of selectively binding one affinity tag and eluting the affinity tag from the affinity resin after substances not bound to the fusion protein have been removed.

In one embodiment, the method further comprises subjecting the purified material of step (f) to mass spectrometry to identify the bound ligand.

This system can also be used to identify conditions or genetic mutations that affect LBD activity. For example, stress, heat, diet, aging etc could all be tested. Similarly, mutations could be crossed in genetically or induced with mutagens or specific RNAi/morpholino constructs to understand genetic pathways that control or respond to ligand binding.

The following non-limiting examples are illustrative of the present invention:

EXAMPLES

Example 1

Zebrafish

Methodology and Results
Construction of a Bifunctional Vector (pLT)

The pLT (Ligand Trap) vector (FIG. 1) has two main components, a fusion protein expression system and a fusion protein-dependent reporter system. The vector backbone is derived from pBluescript II (Stratagene), which contains an Ampicillin resistance gene and T7 and T3 promoters. In the example shown, the fusion protein expression system is comprised of an inducible promoter, followed by multiple (consecutive) affinity tags fused to a minimal Gal4 DNA-binding domain (DBD; amino acids 1-132). Following the DBD are a set of restriction sites (MSC; Pme/Nhe) positioned such that the ligand-binding domain of a NR, or any other potential transcriptional activation motif, can be cloned in frame C-terminal to the Gal4 DBD to complete the transcription factor fusion gene. A Kozak consensus sequence and a start codon were engineered upstream of the tags for efficient translation. An SV40 polyadenylation signal located after the MCS ensures proper transcript termination, processing and translation. The inducible promoter shown is a minimal zebrafish heat shock promoter (min zHSP70), which can be used to induce expression of the tagged-Gal4 DBD-bait fusion in any tissue or stage in the animal's life cycle. This promoter is flanked by unique restriction sites so that it can be exchanged for any other promoter of choice (e.g. tissue-specific promoters). The "triple tag" shown consists of 3×FLAG, Strep II, and 6×His tags. Between the 3×FLAG and the Strep II tag a TEV (tobacco etch virus) cleavage side is engineered.

The reporter part of the ligand trap construct is separated from the fusion protein component by pBluescript II sequence. Unique restrictions sites present in this sequence were used for insertion of the live-animal reporter system. In this case, the reporter is an enhanced green fluorescent protein (eGFP) gene, containing a C-terminal nuclear localization signal (NLS). Multiple DNA binding sites for the Gal4 DBD protein (UAS$_{GAL4}$) are located upstream of the eGFP sequence, followed by a basal adenoviral E1b promoter. The UAS sites are separated form the eGFP coding sequence by a Kozak sequence followed by an ATG start codon. An SV40 polyadenylation signal was placed after the coding sequence of eGFP.

Expression of the GAL4-LBD fusion proteins at inappropriate times or in inappropriate tissues often causes dominant negative phenotypes. This means that fusion protein expression must be kept silent until the transgenic animals are ready for testing. To accomplish this, a minimal heat-inducible promoter was generated that is not leaky, and that provides high levels of GAL4-LBD fusion protein expression upon short elevations of temperature (FIG. 1). Also, to prevent the influence of flanking enhancers and silencers, Drosophila-derived gypsy insulator elements were added to each end of the insertable DNA (FIG. 1).

Flanking the protein fusion and reporter system components are a set of I-SceI meganuclease sites, used for optimal genomic integration of the two-component system, and two insulator elements (gypsy) to prevent the influences of nearby regulatory elements at the sites of genomic insertion.

All recombinant DNA manipulations followed standard procedures (Sambrook et. al., 1989)

Steps of pLT Construction:
1 Cloning of the Gal DNA-binding domain (DBD) fused to the SV40 polyadenylation signal (SV40 pA); plasmid 1
2 Creation of a triple-tag; plasmid 2
3 Introduction of the triple-tag into plasmid 1 resulting in plasmid 3
4 Introduction of two I-SceI meganuclease restriction sites into plasmid 3; resulting in plasmid 4
5 Insertion of eGFP fused to the SV40 pA; plasmid 5
6 Creation of the pLT reporter by cloning Gal4 DBD binding sites (UAS) and a basal promoter (E1b) into plasmid 5; resulting in plasmid 6
7 Integrating the reporter into plasmid 4; resulting in plasmid 7
8 Cloning of a heat shock inducible promoter (zebrafish Hsp70) into plasmid 7; resulting in plasmid 8
9 Integration of two gypsy insulator elements between the I-SceI sites and the ligand trap components, plasmid 9

Plasmid 1 (PB Gal1-132-PA)

To generate pLT we cloned the Gal4 DBD amino acid 1-132 into the pBluescript II (Stratagene) vector (template pBS SK Gal4VP16 SV40pA {Koster, 2001}) containing a SV40 pA tail. PmeI and NheI restriction sites were introduced into the construct as cloning sites for nuclear receptor ligand-binding domains (NR LBDs). An EcoRV restriction site was designed N-terminal of the Gal4 DBD to introduce the triple tag. The resulting vector was named pB Gal1-132-pA.

Oligos used:

(SEQ ID NO: 2)
5'-ATTCATCTAGAGATATCAAGCTACTGTCTTCTATCGAACAAGC (SEQ ID NO: 3)
3'-ATTATCTAGAGTTTAAACAGCTAGCTGATGATGTCGCACTTATTCTA
TGC

Plasmid 2 (pB II Triple Tag):

Triple tag oligos were designed that encode the 3× Flag-Tev-Strep-TagII-6×His tag, and flanked on either site with EcoRI restriction sites. Tev indicates the consensus cleavage site for the tobacco etch virus (TEV) NIa proteinase. Oligos were dissolved in STE Buffer (10 mM Tris pH 8.0, 50 mM NaCl, 1 mM EDTA) and were mixed together in equal molar amounts. The triple-tag oligonucleotides were cloned into EcoRI pBSII KS (Stratagene) producing the plasmid pB II triple-tag.

```
Oligos used:
sense
                                        (SEQ ID NO: 4)
AATTCGACTACAAAGACCATGACGGTGATTATAAAGATCATGACATCGAC

TACAAGGATGACGATGACAAGGAGAACCTGTACTTCCAGTCCAACTGGA

GCCACCCGCAGTTCGAAAAGCATCACCATCACCATCACG antisense
                                        (SEQ ID NO: 5)
ATGATCTTTATAATCACCGTCATGGTCTTTGTAGTCGAGTTGGACTGGAA

GTACAGGTTCTCCTTGTCATCGTCATCCTTGTAGTCGATGTCAATTCGTG

ATGGTGATGGTGATGCTTTTCGAACTGCGGGTGGCTCC.
```

Plasmid 3 (pB Triple Tag-Gal1-132-pA)

The tag was PCR amplified with primers containing EcoRV restriction sites and a Kozak consensus sequence followed by an ATG start codon. This fragment was then introduced into the EcoRV restriction site of pB Gal1-132-pA resulting in pB triple tag-Gal1-132-pA.

```
Oligos used:
                                        (SEQ ID NO: 6)
5'-ATTATGATATCgccaccatgGACTACAAAGACCATGACGG (SEQ ID NO: 7)
3'-ATTATGATATCGTGATGGTGATGGTGATGC
```

Plasmid 4 (SceI pB Triple Tag-Gal1-132-pA)

Next, two I-SceI mega nuclease recognition sites were introduced by site-directed mutagenesis into pB triple tag-Gal1-132-pA. One site was introduced 3' to the T7 promoter and the other site 5' of the T3 promoter on the sense strand. The resulting vector was named SceI pB triple tag-Gal1-132-pA. Correct insertion was verified by digestion.

```
Oligos used:
T7
                                        (SEQ ID NO: 8)
5'-GACTCACTATAGGGCTAGGGATAACAGGGTAATGAATTGGGTACCG

GG

T7
                                        (SEQ ID NO: 9)
3'-CCCGGTACCCAATTCATTACCCTGTTATCCCTAGCCCTATAGTGAG

TC

T3
                                        (SEQ ID NO: 10)
5'-CGGTGGAGCTCCAGTAGGGATAACAGGGTAATCTTTTGTTCCCTTTA

GTG

T3
                                        (SEQ ID NO: 11)
3'-CACTAAAGGGAACAAAAGATTACCCTGTTATCCCTACTGGAGCTCCA

CCG
```

Plasmid 5 (pB eGFP-pA)

The eGFP NIs fragment was PCR amplified from the pUAS Stinger vector {Barolo, 2000} and cloned into the pBluescript II (Stratagene) vector containing a SV40 pA (template pBS SK Gal4VP16 SV40pA {Koster, 2001}). The resulting vector was pB eGFP-pA.

```
Oligos used:
5'-ATTATCTAGAACCATGGTGAGCAAGGGC          (SEQ ID NO: 12)

3'-ATTATCTAGATTACTTGTACAAGTAGCG          (SEQ ID NO: 13)
```

Plasmid 6 (PB UASE1b-eGFP-pA)

A fragment containing multi-UAS Gal DBD binding sites followed by the basal adenovirus promoter E1b was PCR amplified from pBUASEIB {Koster, 2001} and inserted into pB eGFP-pA.

```
Oligos used:
                                        (SEQ ID NO: 14)
5'-ATTATCCGCGGGGTACCCTCCAAGGCGGAGTACTGTCC (SEQ ID NO: 15)
3'-ATAATCGGCCGGTGTGGAGGAGCTCAAAGTGAGGC
```

Plasmid 7 (SceI pB Triple Tag-Gal1-132-pA-UASE1b-eGFP-pA)

The UASE1b-eGFP-pA fragment cut out from plasmid 6 by KpnI digestion and cloned into KpnI digested pB SceI-Tag-Gal1-132-pA (Plasmid 4).

Plasmid 8 (pLT SceI pB zHsp70 Triple Tag Gal-1-132-pA-UASE1b-eGFP-pA)

Plasmid 7 was SacI/NotI cut to insert a SacII/NotI fragment (ca 1500 bp) of the minimal zebrafish Hsp70 promoter amplified from pzHSP70/4prom {Shoji, 1998}.

```
Oligos used:
5'-ATTATCCGCGGTCAGGGGTGTCGCTTGG          (SEQ ID NO: 16)

3'-ATTATGCGGCCGCGATATCGAATTCCTGCAGG      (SEQ ID NO: 17)
```

Plasmid 9 (pLT Gypsy; SceI Gypsy pB zHsp70 Triple Tag Gal-1-132-pA-UASE1 b-eGFP-pA)

The gypsy insulator elements from the *Drosophila* transformation vector UAS-Stinger GFP {Barolo, 2000} were PCR-amplified and inserted upstream of the Hsp70 promoter into SacII restriction sites or downstream of the eGFP reporter into HindIII/ApaI.

```
Oligos used:
                                        (SEQ ID NO: 18)
5'-HSP-ATAACCGCGGTCACGTAATAAGTGTGCG (SEQ ID NO: 19)
3'-HSP-ATAACCGCGGAGATCTATACTAGAATTGATCGGC (SEQ ID NO: 20)
5'-GFP-ATAAAAGCTT TCACGTAATAAGTGTGCG (SEQ ID NO: 21)
3'-GFP-ATAAGGGCCCATACTAGAATTGATCGGC
```

Fish Maintenance and Microinjection of Zebrafish Embryos and Production of Transgenic Zebrafish Lines Adult zebrafish were originally obtained from the Zebrafish International Resource Center (University of Oregon) and maintained in our own fish facility with a controlled light cycle of 14 h light/10 h dark at 28 C. The fish were fed a combination of dry flake food (Tetra brand) and live brine shrimp nauplia, *Artemia salina*. Mating tanks (groups of six females and three males) were set up in the evening and spawned soon after the onset of the light period, and fertilized eggs were collected at the one-cell stage.

To generate permanent transgenic ligand trap lines, 3 nl of pLT plasmid and I-SceI enzyme in 5 mM Tris, 0.5 mM ethylenediamine tetraacetic acid (EDTA), 100 mM KCl and 0.1% phenol red was injected into the blastomeres of early one-cell stage embryos with a glass micropipette. Eggs were incubated at 28° C. in 0.5 E2 media (17.5 g NaCl, 0.75 g KCl, 2.4 g $MgSO_4$, 0.41 g $KH_2PO_4$, 0.12 g $Na_2HPO_4$ to 1 liter of water to make a 20×E2 stock. Add 7.25 g $CaCl_2$ to 100 ml of water. Add 3 g $NaHCO_3$ to 100 ml of water. To make 2 liter of 0.5×E2 combine 50 ml 20×E2 stock, 2 ml of the $CaCl_2$ solution, 2 ml of the $NaHCO_3$ solution) in petri dishes. To ensure that sufficient numbers of transgenic fish were generated, at least 150 fish (F0) were raised to adulthood for each injected construct. F0 fish were then bred with wild type fish, and germline integrated transgenic zebrafish were selected by screening progeny by PCR (at least 100 embryos) using primers against GFP. Reporter positive fish were saved for further analysis and breeding. 100 progeny (F1) of a GFP positive fish were raised to sexual maturation and crossed with other offspring of the GFP positive fish. F2 progeny fish were mated with wild type fish to identify homozygous ligand trap fish (F3). After a founder fish was identified by PCR, other methods, such as Southern blotting and visual examination of reporter activity were performed on the progeny to confirm the identity of the founder fish. Germline transgenic fish obtained from the injected founders have continued to express the ligand trap construct for many generations.

Cell Culture and Temperature Treatments

Cell culture was performed with the zebrafish (*Danio rerio*) embryonic fibroblast cell line, ZF4 (ATCC CRL 2050; {Driever, 1993}), which was originally established from 1-day-old zebrafish embryos. The cells were grown to confluency at 28° C., 5% $CO_2$, in Dulbecco's modified Eagle's medium/F12 nutrient mix (DMEM/F12) supplemented with 10% FBS, 1%-glutamine, 100 u/ml penicillin, 100 µg/ml streptomycin and 0.25 µg/ml Fungizone.

Elevated temperature induces a rapid heat shock transcription factor (HSFs)-mediated expression of heat shock (hsp) genes. This cellular response leads to an expression of the ligand trap construct (triple tag Gal DBD NHR LBD), which if active, then leads to activation of the reporter. Heat shock treatment (37° C.) was performed by incubating cells or animals in a water bath for 1 h. Control cells or animals were incubated in a water bath at 28° C. All cell culture medium components were purchased from Gibco BRL Life Technologies Ltd (USA). Transient transfections were performed using Lipofectamine 2000 (Invitrogen) according to the instructions of the manufacturer.

Detection of Fusion Proteins by Western Blotting

Expression of ligand trap constructs using the pLT system was verified by Western blot. Whole cell extracts were prepared from transfected (cells) or transgenic (animal tissue) cells, and 20 µg protein separated on 10% SDS-polyacrylamide gels and then transferred to nitrocellulose membranes (Schleicher and Schuell, Keene, N.H., USA) using a wet transfer apparatus (Bio-Rad, CA, USA). Membranes were blocked for 1 h in 5% non-fat dry milk in PBS with 0.5% Tween 20. The tagged fusion proteins were detected using a monoclonal mouse anti-M2 antibody (dilution 1:10 000; Sigma). Horseradish-peroxidase-conjugated rabbit anti-mouse immunoglobulin (Amersham Life Sciences, Buckinghamshire, UK) was used as a secondary antibody, and the signals were visualized using enhanced chemiluminescence according to the manufacturer's instructions (Amersham).

Compound Screening

Zebrafish were collected from wild type or transgenic ligand trap fish. Embryos were raised in a 28° C. incubator in 0.5×E2 media in petri-dishes. For ligand screening eggs, embryos, juvenile or adult fish were heat induced (28→37° C.) for 30 min in a water bath. Any developmentally delayed (dead or unfertilized) embryos were removed. Specimens were then combined into clutches of 3-10 and dispensed into multi-well plates in 0.5×E2 media supplemented with 1% DMSO, 0.05 U/ml penicillin, 50 ng/ml streptomycin. For embryos and juvenile fish 1% DMSO is used as a vehicle for small molecules to facilitate solubility and permeability. Chemicals stored in DMSO or ethanol were diluted appropriately and added individually to different wells. The screening concentrations of library compounds ranged from 0.1-20 µM. Compounds were introduced into adult fish via intraperitoneal injection.

Ligand Trap Detection

Ligand trap GFP reporter signal can be monitored in live animals 4-6 h after heat induction. For analyzing GFP fluorescent pattern, embryos, larvae and adult fish were anesthetized with 0.05% 2-phenoxyethanol (Sigma) and GFP expression was examined under a fluorescein isothiocyanate (FITC) filter on a Leica CTR MIC.

Affinity Purification of Proteins and Bound Molecules

Figure 6:
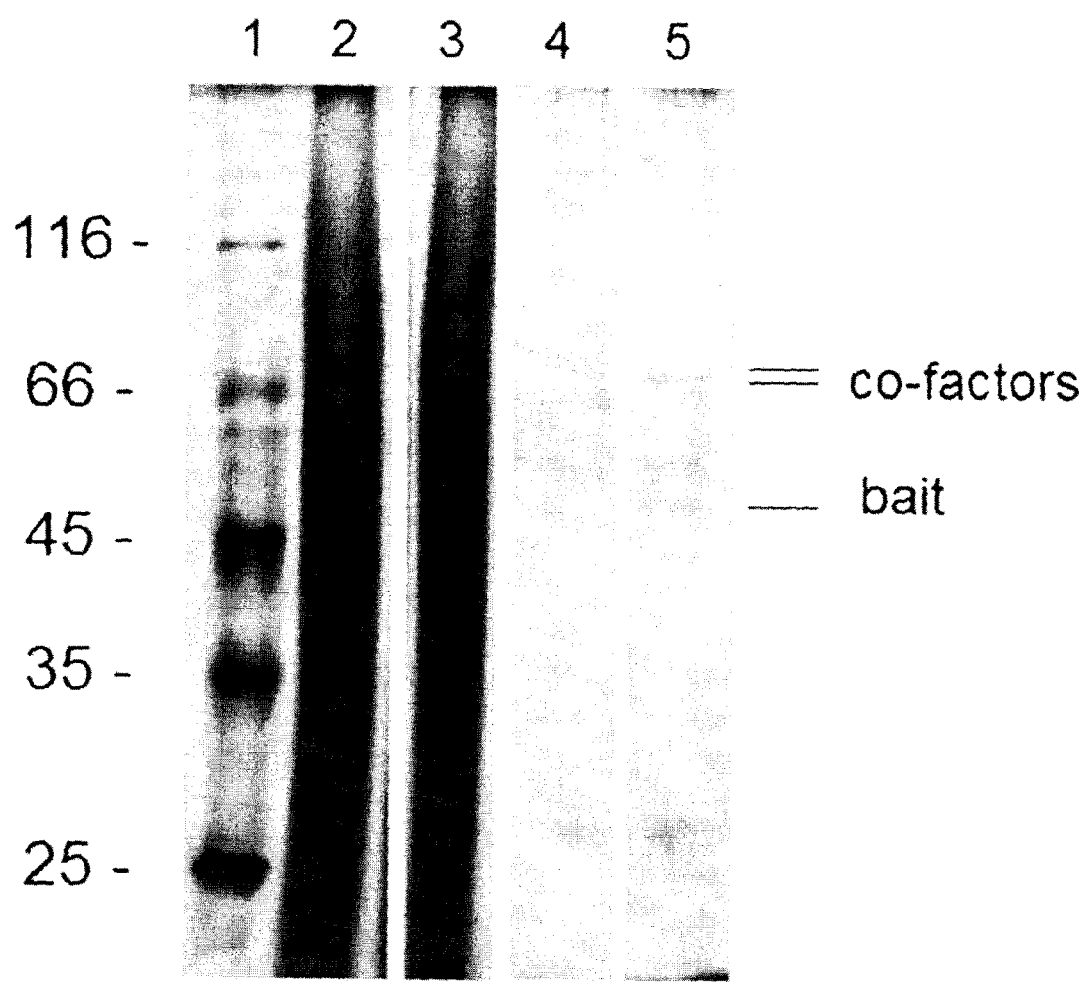
FIG. 6 shows the ability of the triple-tag system to copurify and identify specifically associated ligands. A silver stained SDS PAGE gel was loaded with extract containing the ligand trap fusion protein GAL4-TRβ expressed, in this case, in cultured ZF4 cells. The GAL4-TRβ-containing extract, or mock extract (no TRβ induced), was affinity purified in successive steps using the following resins: FLAG M2 monoclonal antibody matrix (Sigma), Strep-Tactin Superflow (IBA) and finally Talon Superflow metal (Clontech). Beads were extensively washed after each interaction and then bound proteins specifically eluted as specified (see Methods). The starting extract and final elutions were loaded on a 10% SDS gel, and after electrophoresis, silver stained for proteins. Each of the bands seen only in the TRβ "bait" lane was successfully identified using ESI-MS, including the bait protein itself and two previously known cofactors. Lane 1: Marker; Lane 2: mock extract; Lane 3: Gal4-TRβ extract; Lane 4: triple-purified mock eluate; Lane 5: Triple-purified TRβ eluate.
Figure 7:
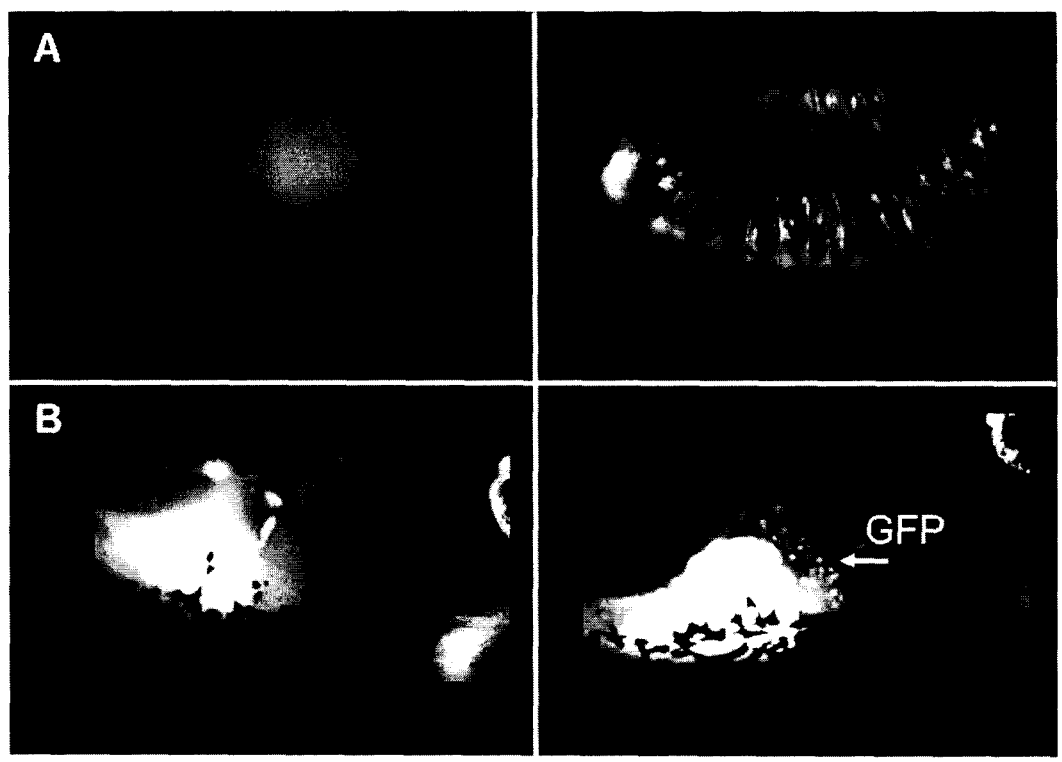
FIG. 7 shows that Ligand Trap lines can be used to screen for activating substances. Panel A shows transgenic Drosophila embryos that express a GAL4-DHR96 (Drosophila hormone receptor 96) fusion protein and a UAS-GFP reporter. The embryo on the left was incubated in control media, and the embryo on the right in $10^{-5}$ molar CITCO. CITCO is a component of a small molecule library used to screen for novel DHR96 ligands. This is the first example of a DHR96-specific ligand (methods described in {Palanker, 2006}). Panel B shows seven day old Thyroid hormone receptors (TRβ) fish embryos grown in the absence (left) or presence (right) of a known TRβ ligand ($10^{-5}$ molar tri-iodothyroacetic acid). Induced GFP expression is seen in the liver and gut of the ligand-treated embryos (arrow). This shows that fish ligand trap lines can also be used for exogenous ligand screening.

Cells or animals were heat induced (37° C.) for 1 h and collected after 12 to 24 h incubation at 28° C. Fish tissue was minced with scissors and all following procedures were performed at 0°-4° C. Lysis of cells or animal tissue was performed for non-denaturing purifications in Flag-Strep buffer (100 mM Tris-Cl, 150 mM NaCl, 10 mM of 2-mercaptoethanol, 0.1% Triton X-100 and 1 Roche complete Mine protease inhibitor cocktail tablet). Extracts were sonicated and centrifuged for 10 min at 9000 rpm in a Beckman centrifuge. Strep II tag and Flag tag incubation and washing was performed in Flag-Strep buffer. FLAG tag elution was done in the same buffer with 100 mg/ml 3×FLAG peptide (Sigma) or in Tev-cleavage buffer (100 mM NaCl, 50 mM Tris-HCl pH 8.0, 0.5 mM EDTA, 1 mM DTT and 1 Roche complete Mine protease inhibitor cocktail tablet) with 0.5 mg TEV for 1 h at 4° C. Strep II tag elution was done in Flag-Strep buffer with 2.5 mM desthiobiotin. For HIS tag incubation and washing His buffer was used (50 mM sodium phosphate, pH 7, 100 mM NaCl, 5 mM of 2-mercaptoethanol, 0.1% Triton X-100 and Roche complete Mine protease inhibitor cocktail tablet) elution was done in the same buffer with 100 mM imidazole. Elutions were performed in gravity feed disposable columns (Bio-Spin columns, Bio-Rad). Resins used were Talon Superflow metal affinity (Clontech), Strep-Tactin Superflow (IBA), FLAG M2 monoclonal antibody matrix (Sigma, catalog). The extracts were incubated with the resin for 30 min (Talon, Strep-Tactin) or 120 min (anti-FLAG). FIG. 6 shows an example of an SDS PAGE gel affinity purification.

MS and HPLC/ESI-MS

To purify ligand trap bait containing complexes for analysis by mass spectrometry, $5×10^8$ pLT-transfected cells (100× 15 cm confluent culture dishes) or 10 g of zebrafish tissue or embryo were lysed and purified as described. Purified samples were precipitated with TCA, separated by SDS/PAGE, and stained with colloidal coomassie blue stain or silver stain (Invitrogen). Individual bands were excised, digested with Trypsin, and analyzed using a quadrupole time-of-flight hybrid tandem mass spectrometer (Q-TOF; Waters-Micromass, Milford, Mass.) equipped with a Micromass Z-type electrospray ionization source.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Table 1

| NRNC Symbol | Name | Full Name | GFP signal | F1/F2 fish |
|---|---|---|---|---|
| NR1A1 | TR α | Thyroid hormone receptor-alpha | B, HS, CNSH, Y | Yes |
| NR1A2 | TR β | Thyroid hormone receptor-beta | B, CNS, H AT,Y | Yes |
| NR 1B1 | RAR α | all-trans Retinoic acid receptor-alpha | B, HS, M, S, ;Y | |
| NR 1B2 | RAR β | all-trans Retinoic acid receptor-beta | B, M, Y | Yes |
| NR 1B3 | RAR γ | all-trans Retinoic acid receptor-gamma | B, Y | |
| NR1C3 | PPAR γ | Peroxisome proliferator-activated receptor-gamma | B, AT, Y, CNS | Yes |
| NR1D1 | Rev-erbA α | Rev-erb alpha | M, Y, B | Yes |
| NR1D2 | Rev-erbA β | Rev-erb beta | B, S, H, CNS, HS, E, Y | Yes |
| NR 1F1 | ROR α | RAR-related orphan receptor-alpha | H, S, Y | Yes |
| NR 1F2 | ROR β | RAR-related orphan receptor-beta | H, HS, CNS, S, Y | Yes |
| NR1F3 | ROR γ | RAR-related orphan receptor-gamma | H, M, S, Y | Yes |
| NR1H3 | LXR α | Liver X receptor alpha | Y, M, B | Yes |
| NR1I1 | VDR | Vitamin D receptor | Y | |
| NR1I3 | CAR | Constitutive androstane receptor | S, M, B, Y | |
| NR 2B1 | RXR α | 9-cis retinoic acid receptor-alpha | B, HS, M, S, ;Y | |
| NR2EI | TLX | | — | |
| NR2E3 | PNR | Photoreceptor cell-specific nuclear receptor | E, Y | |
| NR2F1 | Coup-TFI | Chicken ovalbumin upstream promoter-transcription factor I | — | |
| NR2F6 | EAR2 | erbA-related receptor 2 | Y | |
| NR 3A1 | ER α | Estrogen receptor-alpha | B, M, H, Y | |
| NR3B3 | ERR γ | Estrogen-related receptor gamma | B, M, H, Y | |
| NR3C1 | GR | Glucocorticoid receptor | B, H, HS, H, M, | Yes |
| NR4A1 | NGFI | | S, Y | Yes |
| NR4A2 | Nurr1 | | B, CNS, Y | |
| NR4A3 | NOR1 | Neruon-derived orphan receptor 1 | H, Y | |
| NR5A1 | SF1 | Steroidogenic factor 1 | Y | |
| NR6A1 | GCNF | Germ cell nuclear factor | — | |
| NR0B1 | DAX1 | Dosage-sensitive sex reversal-adrenal hypoplasia congenita critical region on the X chromosome, gene 1 | Y | |
| NR0B2 | SHP | Short heterodimeric partner | — | |

NRNC = 5Nuclear Receptor Nomenclature;
pLT = plasmid Ligand Trap vector;
germl. Fish = ligand trap vector stably integrated in the germline;
B = brain;
M = muscle;
HS = hematopoietic system, blood;
CNS = central nervous system;
S = skin;
H = heart;
AT = white adipose tissue;
Y = Yolk;
E = Eye

TABLE 2

SceI Gypsy(Insulator)zHSP70 Fest-Gall-132-pA-UASE1B-eGFp-pA

```
  1 ATTACCCTGT TATCCCTACT GGAGCTCCAC CGCGGTCACG TAATAAGTGT SceI

51 GCGTTGAATT TATTCGCAAA AACATTGCAT ATTTTCGGCA AAGTAAAATT
    Insulator

101 TTGTTGCATA CCTTATCAAA AAATAAGTGC TGCATACTTT TTAGAGAAAC

151 CAAATAATTT TTTATTGCAT ACCCGTTTTT AATAAAATAC ATTGCATACC
    Insulator

201 CTCTTTTAAT AAAAAATATT GCATACTTTG ACGAAACAAA TTTTCGTTGC

251 ATACCCAATA AAAGATTATT ATATTGCATA CCCGTTTTTA ATAAAATACA
    Insulator

301 TTGCATACCC TCTTTTAATA AAAAATATTG CATACGTTGA CGAAACAAAT

351 TTTCGTTGCA TACCCAATAA AAGATTATTA TATTGCATAC CTTTTCTTGC
    Insulator

BglII
401 CATACCATTT AGCCGATCAA TTAGATCTCC GCGGTCAGGG GTGTCGCTTG

451 GTTATTTCCA AAAATCAAAT TAATTTTATT AAACTATTAG AACGAGCATG HSP
```

TABLE 2-continued

SceI Gypsy(Insulator)zHSP70 Fest-Gal1-132-pA-UASE1B-eGFp-pA

```
 501 TTTTGTCTAT ATGCTACAGA AGATAAAAAA TAATAGGAGT TAACAGTTAT
 551 AAAACAACAC ATTTGTTTCT ATTGATTGTT GACCACACTG GGGTCTCATT
 601 AAGTTAGATT AAAGACACAC TAACTGGGTC AAAAGCAGCA GATTGATTTC
 651 ATAGCACCAG GGTAAACTTT CTAACACTTT TACGGCAATC ATATACATTA   HSP
 701 AAATTAAATA CAGACCACGA CTGAACAAGG AGGATGATCT CCAATATTAA
 751 ACAAAGAGAC TTGTGCCTAT TTCTCTGAGG GTAAACATGA CCTCTCAAGT
 801 TAGCAAGTTG TTTTTAACAC TACAAAAATA GTTAAGACCT GCAATCCCAG
 851 AATAAAGTAT TGGTTTTAAC CAATCAATAT AGTACAGTAA ACATCCATTT   HSP
 901 GTTTTGTTGA AACGTTAAAC AAATCTGACC AAAGCTATTA GCTTATATAA
 951 AACAGGTTTG CCTTCTATGT AGCTGAAAAC ACCACAGGCC CGATTTTGCT
1001 ACTGTGTAAA ACATTTCAGC AAGATTTTTT TATTGCATTT TTTTTTACTG
1051 AATCGTTCAA ACATTTTATC ATTTTAGTTT GTTCATTCAT TGCAACTGGA   HSP
1101 AAAACAACAC ATCACACAAC CGCACATATT TCAGCAATAA GTACAATAAA
1151 ACACTCAAAT AAAAAAAACA TTTTAAATCT CTTTGTATTT TTGACCGCTG
1201 TTTCGCGTAA TTTCACGGTA AAACTCTGGA AATCTCCACT ACATTCCTCT
1251 CAGCGGCTCC TCTCAATGAC AGCTGAAGAA GTGACGGCGG CTGCCTGCTG   HSP
1301 TGTTTTGATT GGTCGAATTC ACTGGAGGCT TCCAGAACAG TGTAGAGTCT
1351 GAACGGGTGC GCGCTCTGCT GTATTTAAAG GGCGAAAGAG AGACCGCAGA
1401 GAAACTCAAC CGAAGAGAAG CGACTTGACA AGAAGAAAA GAGCAGCCTG
1451 ACAGGACTTT TCCCCGACGA GGTGTTTATT CGCTCTATTT AAGAATCTAC   HSP
1501 TGTAAGGTAA GTCTCAATAT ATTGTACTCT ATTGGCTAAT CAGAATTATA
1551 TAGAGATTAT ATGTACTTAA TGTCAAAAAA TCAACTTTGT ATATGTAATC
1601 TTTTTACATG TGGACTGCCT ATGTTCATCT TATTTTAGGT CTACTAGAAA
1651 ATTATATTTC CCGTTTTCAC AATAAGGATT TTAAAAAAG CAATGAACAG   HSP
1701 ACGGGCATTT ACTTTATGTT GCTGACATTA TTTTATATGA GCATAATAAC
1751 CATAAATACT AGCAAATGTC CTAAATGAAT TTGTGTTAAT GTTGTCTACA
1801 AAAGAAAATT AGCGTTTTAC TTGTACAACT AATAATAACT TGGTTATTAA
1851 GAGAATTTCA CTTGTTGACT AGAAAATCC TTTCATAATG AAACAATTGC   HSP
1901 ACCGATAAAT TGTATAAATA TAAAATTAAT TCTAATTGTT TTTTTTTTC
                   EcoRV  NotI           EcoRV
1951 CTGCAGGAAT TCGATATCGC GGCCGCTCTA GAGATATCGC CACCATGGAC
                                                       M  D  3x
     Flag
2001 TACAAAGACC ATGACGGTGA TTATAAAGAT CATGACATCG ACTACAAGGA
      Y  K  D  H  D  G  D  Y  K  D  H  D  I  D  Y  K  D  Tev 2051 TGACGATGAC AAGGAGAACC TGTACTTCCA GTCCAACTGG AGCCACCCGC   Strep
      D  D  D  K  E  N  L  Y  F  Q  S  N  W  S  H  P  Q
                                   EcoRV
2101 AGTTCGAAAA GCATCACCAT CACCATCACG ATATCAAGCT ACTGTCTTCT
      F  E  K  H  H  H  H  H  H  D  I  K  L  L  S  S    6xHis 2151 ATCGAACAAG CATGCGATAT TTGCCGACTT AAAAAGCTCA AGTGCTCCAA
      I  E  Q  A  C  D  I  C  R  L  K  K  L  K  C  S  K  Gal
                                                          DBD
```

TABLE 2-continued

SceI Gypsy(Insulator)zHSP70 Fest-Gal1-132-pA-UASE1B-eGFp-pA

```
2201 AGAAAAACCG AAGTGCGCCA AGTGTCTGAA GAACAACTGG GAGTGTCGCT
      E  K  P    K  C  A  K    C  L  K    N  N  W    E  C  R  Y

2251 ACTCTCCCAA AACCAAAAGG TCTCCGCTGA CTAGGGCACA TCTGACAGAA
      S  P  K    T  K  R    S  P  L  T    R  A  H    L  T  E

2301 GTGGAATCAA GGCTAGAAAG ACTGGAACAG CTATTTCTAC TGATTTTTCC
      V  E  S  R    L  E  R    L  E  Q    L  F  L  L    I  F  P

2351 TCGAGAAGAC CTTGACATGA TTTTGAAAAT GGATTCTTTA CAGGATATAA
      R  E  D    L  D  M  I    L  K  M    D  S  L    Q  D  I  K

2401 AAGCATTGTT AACAGGATTA TTTGTACAAG ATAATGTGAA TAAAGATGCC
      A  L  L    T  G  L    F  V  Q  D    N  V  N    K  D  A

2451 GTCACAGATA GATTGGCTTC AGTGGAGACT GATATGCCTC TAACATTGAG
      V  T  D  R    L  A  S    V  E  T    D  M  P  L    T  L  R

NheI        PmeI
2501 ACAGCATAGA ATAAGTGCGA CATCATCAGC TAGCTGTTTA AACTCTAGAA  (SEQ ID NO: 22)
      Q  H  R    I  S  A  T    S  S

2551 CTATAGTGAG TCGTATTACG TAGATCCAGA CATGATAAGA TACATTGATG  SV40 pA

2601 AGTTTGGACA AACCACAACT AGAATGCAGT GAAAAAAATG CTTTATTTGT

2651 GAAATTTGTG ATGCTATTGC TTTATTTGTA ACCATTATAA GCTGCAATAA  SV40pA

2701 ACAAGTTAAC AACAACAATT GCATTCATTT TATGTTTCAG GTTCAGGGGG

ClaI
2751 AGGTGTGGGA GGTTTTTTAA TTCGCGGCCA TCAAGCTTAT CGATACCGTC

KpnI
2801 GACCTCGAGG GGGGGCCCGG TACCCTCCAA GGCGGAGTAC TGTCCTCCGG

2851 GCTGGCGGAG TACTGTCCTC CGGCAAGGTC GGAGTACTGT CCTCCGACAC  UAS

2901 TAGAGGTCGG AGTACTGTCC TCCGACGCAA GGCGGAGTAC TGTCCTCCGG

2951 GCTGCGGAGT ACTGTCCTCC GGCAAGGTCG GAGTACTGTC CTCCGACACT  UAS

3001 AGAGGTCGGA GTACTGTCCT CCGACGCAAG GTCGGAGTAC TGTCCTCCGA

3051 CACTAGAGGT CGGAGTACTG TCCTCCGACG CAAGGTCGGA GTACTGTCCT

3101 CCGACACTAG AGGTCGGAGT ACTGTCCTCC GACGCAAGGC GGAGTACTGT  E1b

3151 CCTCCGGGCT GGCGGAGTAC TGTCCTCCGG CAAGGGTCGA CTCTAGAGGG

3201 TATATAATGG ATCCCATCGC GTCTCAGCCT CACTTTGAGC TCCTCCACAC

3251 CGGCCGCTCT AGAATGGTGA GCAAGGGCGA GGAGCTGTTC ACCGGGGTGG
                          M  V  S  K  G  E    E  L  F    T  G  V  V

3301 TGCCCATCCT GGTCGAGCTG GACGGCGACG TAAACGGCCA CAAGTTCAGC
      P  I  L    V  E  L    D  G  D    V  N  G  H    K  F  S    GFP

3351 GTGTCCGGCG AGGGCGAGGG CGATGCCACC TACGGCAAGC TGACCCTGAA
      V  S  G  E    G  E  G    D  A  T    Y  G  K  L    T  L  K

3401 GTTCATCTGC ACCACCGGCA AGCTGCCCGT GCCCTGGCCC ACCCTCGTGA
      F  I  C    T  T  G  K    L  P  V    P  W  P    T  L  V  T  GFP

3451 CCACCCTGAC CTACGGCGTG CAGTGCTTCA GCCGCTACCC CGACCACATG
      T  L  T    Y  G  V    Q  C  F  S    R  Y  P    D  H  M

3501 AAGCAGCACG ACTTCTTCAA GTCCGCCATG CCCGAAGGCT ACGTCCAGGA
      K  Q  H  D    F  F  K    S  A  M    P  E  G  Y    V  Q  E  GFP

3551 GCGCACCATC TTCTTCAAGG ACGACGGCAA CTACAAGACC CGCGCCGAGG
      R  T  I    F  F  K  D    D  G  N    Y  K  T    R  A  E  V

3601 TGAAGTTCGA GGGCGACACC CTGGTGAACC GCATCGAGCT GAAGGGCATC
      K  F  E    G  D  T    L  V  N  R    I  E  L    K  G  I  GFP

3651 GACTTCAAGG AGGACGGCAA CATCCTGGGG CACAAGCTGG AGTACAACTA
      D  F  K  E    D  G  N    I  L  G    H  K  L  E    Y  N  Y
```

TABLE 2-continued

SceI Gypsy(Insulator)zHSP70 Fest-Gal1-132-pA-UASE1B-eGFp-pA

```
3701 CAACAGCCAC AACGTCTATA TCATGGCCGA CAAGCAGAAG AACGGCATCA
      N  S  H   N  V  Y  I   M  A  D    K  Q  K     N  G  I  K GFP

3751 AGGTGAACTT CAAGATCCGC CACAACATCG AGGACGGCAG CGTGCAGCTC
      V  N  F    K  I  R    H  N  I    E  D  G  S   V  Q  L

3801 GCCGACCACT ACCAGCAGAA CACCCCCATC GGCGACGGCC CCGTGCTGCT
      A  D  H  Y   Q  Q  N    T  P  I    G  D  G  P    V  L  L GFP

3851 GCCCGACAAC CACTACCTGA GCACCCAGTC CGCCCTGAGC AAAGACCCCA
      P  D  N    H  Y  L  S   T  Q  S    A  L  S    K  D  P  N

3901 ACGAGAAGCG CGATCACATG GTCCTGCTGG AGTTCGTGAC CGCCGCCGGG
      E  K  R    D  H  M    V  L  L  E   F  V  T    A  A  G  GFP

3951 ATCACTCTCG GCATGGACGA GCTGTACAAG AGCAGGCACA GAAGGCATCG
      I  T  L  G   M  D  E    L  Y  K    S  R  H    R  R  H  R

4001 CCAGCGCTCT AGGAGCCGCA ATCGCAGCCG AAGTCGCAGC AGTGAACGAA
      Q  R  S    R  S  R  N   R  S  R    S  R  S    S  E  R  K GFP
      NLS

4051 AACGCCGTCA ACGGAGCCGA AGTCGCAGCA GTGAACGAAG ACGCTACTTG
      R  R  Q    R  S  R    S  R  S  S   E  R  R    R  Y  L

4101 TACAAGTAAT CTAGAACTAT AGTGAGTCGT ATTACGTAGA TCCAGACATG  (SEQ ID NO: 23)
      Y  K  *                                              GFP-
      NLS

4151 ATAAGATACA TTGATGAGTT TGGACAAACC ACAACTAGAA TGCAGTGAAA

4201 AAAATGCTTT ATTTGTGAAA TTTGTGATGC TATTGCTTTA TTTGTAACCA

4251 TTATAAGCTG CAATAAACAA GTTAACAACA ACAATTGCAT TCATTTTATG

4301 TTTCAGGTTC AGGGGGAGGT GTGGGAGGTT TTTTAATTCG CGGCCATCAA

4351 GCTTTCACGT AATAAGTGTG CGTTGAATTT ATTCGCAAAA ACATTGCATA
         Insulator

4401 TTTTCGGCAA AGTAAAATTT TGTTGCATAC CTTATCAAAA AATAAGTGCT

4451 GCATACTTTT TAGAGAAACC AAATAATTTT TTATTGCATA CCCGTTTTTA
         Insulator

4501 ATAAAATACA TTGCATACCC TCTTTTAATA AAAAATATTG CATACTTTGA

4551 CGAAACAAAT TTTCGTTGCA TACCCAATAA AAGATTATTA TATTGCATAC
         Insulator

4601 CCGTTTTTAA TAAAATACAT TGCATACCCT CTTTTAATAA AAAATATTGC

4651 ATACGTTGAC GAAACAAATT TTCGTTGCAT ACCCAATAAA AGATTATTAT
         Insulator

4701 ATTGCATACC TTTTCTTGCC ATACCATTTA GCCGATCAAT TCTAGTATGG

KpnI                                       (SEQ ID NO: 1)
4751 GCCCGGTACC CAATTCATTA CCCTGTTATC CCTA           SceI
```

References

Auger, A. P., Tetel, M. J., and McCarthy, M. M. (2000). Steroid receptor coactivator-1 (SRC-1) mediates the development of sex-specific brain morphology and behavior. Proc Natl Acad Sci USA 97, 7551-7555.

Barolo, S., Carver, L. A., and Posakony, J. W. (2000). GFP and beta-galactosidase transformation vectors for promoter/enhancer analysis in *Drosophila*. Biotechniques 29, 726, 728, 730, 732.

Basu-Modak, S., Braissant, O., Escher, P., Desvergne, B., Honegger, P., and Wahli, W. (1999). Peroxisome proliferator-activated receptor beta regulates acyl-CoA synthetase 2 in reaggregated rat brain cell cultures. Biol Chem 274, 35881-35888.

Beuschlein, F., Keegan, C. E., Bavers, D. L., Mutch, C., Hutz, J. E., Shah, S., Ulrich-Lai, Y. M., Engeland, W. C., Jeffs, B., Jameson, J. L., and Hammer, G. D. (2002). SF-1, DAX-1, and acid: molecular determinants of adrenocortical growth and steroidogenesis. Endocr Res 28, 597-607.

Bledsoe, R. K., Montana, V. G., Stanley, T. B., Delves, C. J., Apolito, C. J., McKee, D. D., Consler, T. G., Parks, D. J., Stewart, E. L., Willson, T. M., et al. (2002). Crystal structure of the glucocorticoid receptor ligand binding domain reveals a novel mode of receptor dimerization and coactivator recognition. Cell 110, 93-105.

Bogan, A. A., Cohen, F. E., and Scanlan, T. S. (1998). Natural ligands of nuclear receptors have conserved volumes. Nat Struct Biol 5, 679-681.

Bogan, A. A., Dallas-Yang, Q., Ruse, M. D., Maeda, Y., Jiang, G., Nepomuceno, L., Scanlan, T. S., Cohen, F. E., and Sladek, F. M. (2000). Analysis of protein dimerization and ligand binding of orphan receptor HNF4alpha. J Mol Biol 302, 831-851.

Bolt, R. J., van Weissenbruch, M. M., Lafeber, H. N., and Delemarre-van de Waal, H. A. (2001). Glucocorticoids and lung development in the fetus and preterm infant. Pediatr Pulmonol 32, 76-91.

Bury, N. R., Sturm, A., Le Rouzic, P., Lethimonier, C., Ducouret, B., Guiguen, Y., Robinson-Rechavi, M., Laudet, V., Rafestin-Oblin, M. E., and Prunet, P. (2003). Evidence for two distinct functional glucocorticoid receptors in teleost fish. J Mol Endocrinol 31, 141-156.

Chawla, A., Repa, J. J., Evans, R. M., and Mangelsdorf, D. J. (2001). Nuclear receptors and lipid physiology: opening the X-files. Science 294, 1866-1870.

Davidson, A. E., Balciunas, D., Mohn, D., Shaffer, J., Hermanson, S., Sivasubbu, S., Cliff, M. P., Hackett, P. B., and Ekker, S. C. (2003). Efficient gene delivery and gene expression in zebrafish using the Sleeping Beauty transposon. Dev Biol 263, 191-202.

Day, R. N. (1998). Visualization of Pit-1 transcription factor interactions in the living cell nucleus by fluorescence resonance energy transfer microscopy. Mol Endocrinol 12, 1410-1419.

Degos, L., Dombret, H., Chomienne, C., Daniel, M. T., Miclea, J. M., Chastang, C., Castaigne, S., and Fenaux, P. (1995). All-trans-retinoic acid as a differentiating agent in the treatment of acute promyelocytic leukemia. Blood 85, 2643-2653.

Dhe-Paganon, S., Duda, K., Iwamoto, M., Chi, Y. I., and Shoelson, S. E. (2002). Crystal structure of the HNF4 alpha ligand binding domain in complex with endogenous fatty acid ligand. J Biol Chem 277, 37973-37976.

Dias, J. M., Go, N. F., Hart, C. P., and Mattheakis, L. C. (1998). Genetic recombination as a reporter for screening steroid receptor agonists and antagonists. Anal Biochem 258, 96-102.

Driever, W., and Rangini, Z. (1993). Characterization of a cell line derived from zebrafish (*Brachydanio rerio*) embryos. In Vitro Cell Dev Biol Anim 29A, 749-754.

Egea, P. F., Mitschler, A., Rochel, N., Ruff, M., Chambon, P., and Moras, D. (2000). Crystal structure of the human RXRalpha ligand-binding domain bound to its natural ligand: 9-cis retinoic acid. Embo J 19, 2592-2601.

Francis, G. A., Fayard, E., Picard, F., and Auwerx, J. (2003). Nuclear receptors and the control of metabolism. Annu Rev Physiol 65, 261-311.

Gampe, R. T., Montana, V. G., Lambert, M. H., Miller, A. B., Bledsoe, R. K., Milburn, M. V., Kliewer, S. A., Willson, T. M., and Xu, H. E. (2000). Asymmetry in the PPARgamma/RXRalpha crystal structure reveals the molecular basis of heterodimerization among nuclear receptors. Mol Cell 5, 545-555.

Glass, C. K., and Rosenfeld, M. G. (2000). The coregulator exchange in transcriptional functions of nuclear receptors. Genes Dev 14, 121-141.

Glickman, J. F., Wu, X., Mercuri, R., lily, C., Bowen, B. R., He, Y., and Sills, M. (2002). A comparison of ALPHAScreen, TR-FRET, and TRF as assay methods for FXR nuclear receptors. J Biomol Screen 7, 3-10.

Grover, G. S., Turner, B. A., Parker, C. N., Meier, J., Lala, D. S., and Lee, P. H. (2003). Multiplexing nuclear receptors for agonist identification in a cell-based reporter gene high-throughput screen. J Biomol Screen 8, 239-246.

Hawkins, M. B., Thornton, J. W., Crews, D., Skipper, J. K., Dotte, A., and Thomas, P. (2000). Identification of a third distinct estrogen receptor and reclassification of estrogen receptors in teleosts. Proc Natl Acad Sci USA 97, 10751-10756.

Huss, J. M., Kopp, R. P., and Kelly, D. P. (2002). Peroxisome proliferator-activated receptor coactivator-1 alpha (PGC-1 alpha) coactivates the cardiac-enriched nuclear receptors estrogen-related receptor-alpha and -gamma. Identification of novel leucine-rich interaction motif within PGC-1alpha. J Biol Chem 277, 40265-40274.

Kawakami, K., Shima, A., and Kawakami, N. (2000). Identification of a functional transposase of the Tol2 element, an Ac-like element from the Japanese medaka fish, and its transposition in the zebrafish germ lineage. Proc Natl Acad Sci USA 97, 11403-11408.

Kersten, S., Desvergne, B., and Wahli, W. (2000). Roles of PPARs in health and disease. Nature 405, 421-424.

Kim, R. Y., and Stern, W. H. (1990). Retinoids and butyrate modulate fibroblast growth and contraction of collagen matrices. Invest Opthalmol V is Sci 31, 1183-1186.

Kliewer, S. A., Goodwin, B., and Willson, T. M. (2002). The nuclear pregnane X receptor: a key regulator of xenobiotic metabolism. Endocr Rev 23, 687-702.

Kliewer, S. A., Lehmann, J. M., Milburn, M. V., and Willson, T. M. (1999). The PPARs and PXRs: nuclear xenobiotic receptors that define novel hormone signaling pathways. Recent Prog Horm Res 54, 345-367; discussion 367-348.

Kliewer, S. A., and Willson, T. M. (2002). Regulation of xenobiotic and bile acid metabolism by the nuclear pregnane X receptor. J Lipid Res 43, 359-364.

Kloas, W., Schrag, B., Ehnes, C., and Segner, H. (2000). Binding of xenobiotics to hepatic estrogen receptor and plasma sex steroid binding protein in the teleost fish, the common carp (*Cyprinus carpio*). Gen Comp Endocrinol 119, 287-299.

Koster, R. W., and Fraser, S. E. (2001). Tracing transgene expression in living zebrafish embryos. Dev Biol 233, 329-346.

Kumar, R., and Thompson, E. B. (1999). The structure of the nuclear hormone receptors. Steroids 64, 310-319.

Lee, M. A., Lee, H. S., Cho, K. G., Jin, B. K., Sohn, S., Lee, Y. S., Ichinose, H., and Kim, S. U. (2002). Overexpression of midbrain-specific transcription factor Nurr1 modifies susceptibility of mouse neural stem cells to neurotoxins. Neurosci Lett 333, 74-78.

Llopis, J., Westin, S., Ricote, M., Wang, Z., Cho, C. Y., Kurokawa, R., Mullen, T. M., Rose, D. W., Rosenfeld, M. G., Tsien, R. Y., et al. (2000). Ligand-dependent interactions of coactivators steroid receptor coactivator-1 and peroxisome proliferator-activated receptor binding protein with nuclear hormone receptors can be imaged in live cells and are required for transcription. Proc Natl Acad Sci USA 97, 4363-4368.

Maglich, J. M., Caravella, J. A., Lambert, M. H., Willson, T. M., Moore, J. T., and Ramamurthy, L. (2003). The first completed genome sequence from a teleost fish (*Fugu rubripes*) adds significant diversity to the nuclear receptor superfamily. Nucleic Acids Res 31, 4051-4058.

Mangelsdorf, D. J., Thummel, C., Beato, M., Herrlich, P., Schutz, G., Umesono, K., Blumberg, B., Kastner, P., Mark, M., Chambon, P., and et al. (1995). The nuclear receptor superfamily: the second decade. Cell 83, 835-839.

McElreavey, K., and Fellous, M. (1999). Sex determination and the Y chromosome. Am J Med Genet. 89, 176-185.

Muddana, S. S., and Peterson, B. R. (2003). Fluorescent cellular sensors of steroid receptor ligands. Chembiochem 4, 848-855.

Osborne, C. K., Zhao, H., and Fuqua, S. A. (2000). Selective estrogen receptor modulators: structure, function, and clinical use. J Clin Oncol 18, 3172-3186.

Palanker, L., Necakov, A. S., Sampson, H. M., Ni, R., Hu, C., Thummel, C. S., and Krause, H. M. (2006). Dynamic regulation of Drosophila nuclear receptor activity in vivo. Development 133, 3549-3562.

Pardee, K., et. al., (2004). Nuclear Hormone Receptors, Metabolism, and Aging: What Goes Around Comes Around.

Rawal, N., Periquet, M., Durr, A., de Michele, G., Bonifati, V., Teive, H. A., Raskin, S., Guimaraes, J., Agid, Y., and Brice, A. (2002). Exclusion of the Nurr1 gene in autosomal recessive Parkinson's disease. J Neurol 249, 1127-1129.

Renaud, J. P., Rochel, N., Ruff, M., Vivat, V., Chambon, P., Gronemeyer, H., and Moras, D. (1995). Crystal structure of the RAR-gamma ligand-binding domain bound to all-trans retinoic acid. Nature 378, 681-689.

Repa, J. J., and Mangelsdorf, D. J. (2002). The liver X receptor gene team: Potential new players in atherosclerosis. Nat Med 8, 1243-1248. Sambrook, E. F. Fritsch and T. Maniatis, Molecular Cloning: a Laboratory Manual 2nd edition. Cold Spring Harbor Laboratory Press. USA, 1989

Satoh, J., and Kuroda, Y. (2002). The constitutive and inducible expression of Nurr1, a key regulator of dopaminergic neuronal differentiation, in human neural and non-neural cell lines. Neuropathology 22, 219-232.

Serhan, C. N., and Devchand, P. R. (2001). Novel antiinflammatory targets for asthma. A role for PPARgamma? Am J Respir Cell Mol Biol 24, 658-661.

Shoji, W., Yee, C. S., and Kuwada, J. Y. (1998). Zebrafish semaphorin Z1a collapses specific growth cones and alters their pathway in vivo. Development 125, 1275-1283.

Stoilov, I., Jansson, I., Sarfarazi, M., and Schenkman, J. B. (2001). Roles of cytochrome p450 in development. Drug Metabol Drug Interact 18, 33-55.

Tetel, M. J. (2000). Nuclear receptor coactivators in neuroendocrine function. Neuroendocrinol 12, 927-932.

Thermes, V., Grabher, C., Ristoratore, F., Bourrat, F., Choulika, A., Wittbrodt, J., and Joly, J. S. (2002). I-SceI meganuclease mediates highly efficient transgenesis in fish. Mech Dev 118, 91-98.

Tonetti, D. A., and Jordan, V. C. (1999). The estrogen receptor: a logical target for the prevention of breast cancer with antiestrogens. J Mammary Gland Biol Neoplasia 4, 401-413.

Turnamian, S. G., and Binder, H. J. (1990). Aldosterone and glucocorticoid receptor-specific agonists regulate ion transport in rat proximal colon. Am J Physiol 258, G492-498.

Uppenberg, J., Svensson, C., Jaki, M., Bertilsson, G., Jendeberg, L., and Berkenstam, A. (1998). Crystal structure of the ligand binding domain of the human nuclear receptor PPARgamma. J Biol Chem 273, 31108-31112.

Wagner, R. L., Apriletti, J. W., McGrath, M. E., West, B. L., Baxter, J. D., and Fletterick, R. J. (1995). A structural role for hormone in the thyroid hormone receptor. Nature 378, 690-697.

Wakino, S., Law, R. E., and Hsueh, W. A. (2002). Vascular protective effects by activation of nuclear receptor PPAR-gamma. J Diabetes Complications 16, 46-49.

Way, J. M., Gorgun, C. Z., Tong, Q., Uysal, K. T., Brown, K. K., Harrington, W. W., Oliver, W. R., Jr., Willson, T. M., Kliewer, S. A., and Hotamisligil, G. S. (2001). Adipose tissue resistin expression is severely suppressed in obesity and stimulated by peroxisome proliferator-activated receptor gamma agonists. J Biol Chem 276, 25651-25653.

Weatherman, R. V., Chang, C. Y., Clegg, N. J., Carroll, D. C., Day, R. N., Baxter, J. D., McDonnell, D. P., Scanlan, T. S., and Schaufele, F. (2002). Ligand-selective interactions of ER detected in living cells by fluorescence resonance energy transfer. Mol Endocrinol 16, 487-496.

Willson, T. M., and Kliewer, S. A. (2002). PXR, CAR and drug metabolism. Nat Rev Drug Discov 1, 259-266.

Willson, T. M., Lambert, M. H., and Kliewer, S. A. (2001). Peroxisome proliferator-activated receptor gamma and metabolic disease. Annu Rev Biochem 70, 341-367.

Xie, W., Barwick, J. L., Simon, C. M., Pierce, A. M., Safe, S., Blumberg, B., Guzelian, P. S., and Evans, R. M. (2000). Reciprocal activation of xenobiotic response genes by nuclear receptors SXR/PXR and CAR. Genes Dev 14, 3014-3023.

Zhao, L., Bakke, M., Krimkevich, Y., Cushman, L. J., Parlow, A. F., Camper, S. A., and Parker, K. L. (2001). Steroidogenic factor 1 (SF1) is essential for pituitary gonadotrope function. Development 128, 147-154.

Zhou, C., Qiu, Y., Pereira, F. A., Crair, M. C., Tsai, S. Y., and Tsai, M. J. (1999). The nuclear orphan receptor COUP-TFI is required for differentiation of subplate neurons and guidance of thalamocortical axons. Neuron 24, 847-859.

Zhu, Y. J., Crawford, S. E., Stellmach, V., Dwivedi, R. S., Rao, M. S., Gonzalez, F. J., Qi, C., and Reddy, J. K. (2003). Coactivator PRIP, the Peroxisome Proliferator-activated Receptor-interacting Protein, Is a Modulator of Placental, Cardiac, Hepatic, and Embryonic Development. Biol Chem 278, 1986-1990.

---

We claim:

1. A composition comprising
   (a) a first nucleic acid comprising an inducible promoter and encoding a fusion protein of a DNA-binding domain, a small molecule hormone-binding domain and at least three different affinity tags that act in succession and are sufficient for purification and subsequent identification of bound small molecules; and
   (b) a second nucleic acid encoding a reporter system, said second nucleic acid comprising a promoter having multiple binding sites for the DNA-binding domain and encoding a fluorescent reporter protein detectable in live animals.

2. The composition of claim 1, wherein the DNA-binding domain is Gal4.

3. The composition of claim 1, wherein the small molecule hormone-binding domain is derived from a Nuclear Receptor protein.

4. The composition of claim 1, wherein the at least three different affinity tags are Strep11, His and FLAG.

5. The composition of claim 1, wherein the inducible promoter is heat, transcription factor or hormone activated.

6. The composition of claim 1, wherein the fluorescent reporter protein is selected from the group consisting of green fluorescent protein, red fluorescent protein, DS-red and luciferase.

7. The composition of claim 6, wherein the fluorescent reporter protein is nuclear, enhanced green fluorescent protein.

8. The composition of claim 1, wherein the first and second nucleic acids are on a single vector.

9. The composition of claim 8, wherein the single vector comprises the nucleotide sequence as shown in SEQ ID NO:1.

10. A method for purifying a modulator of a reporter system, the method comprising:
    (a) providing an animal, said animal having the first and second nucleic acids of the composition of claim 1 transiently expressed or incorporated into its genome;
    (b) inducing expression of the first nucleic acid;
    (c) detecting a signal;
    (d) generating a cellular extract from the animal; and
    (e) subjecting the cellular extract generated in step (d) to multiple affinity purification steps, each step comprising binding one affinity tag to an affinity resin capable of selectively binding one affinity tag and eluting the affinity tag from the affinity resin after substances not bound to the fusion protein have been removed.

11. The method of claim 10, further comprising subjecting the purified substance of step (e) to MALDI-TOV, ESI, GC or semi non-denaturing mass spectrometry.

12. The method of claim 10, further comprising prior to b)
    (a) contacting the animal with a test compound.

13. The composition of claim 1, wherein the DNA-binding domain is unlikely to recognize host protein and DNA sequences.

14. The composition of claim 1, wherein each affinity tag provides at least 1000-fold purification with at least 50% yield activity.

15. The method of claim 10, wherein the animal is selected from the group consisting of *C. elegans, Drosophila, Xenopus*, mouse and zebrafish.

16. A composition comprising
    (a) a first nucleic acid comprising an inducible zebrafish promoter and encoding a fusion protein of a DNA-binding domain, a small molecule hormone-binding domain and at least three different affinity tags that act in succession and are sufficient for purification and subsequent identification of bound small molecules; and
    (b) a second nucleic acid encoding a reporter system, said second nucleic acid comprising a promoter having multiple binding sites for the DNA-binding domain and encoding a reporter protein; wherein the reporter protein is detectable in live animals.

17. The composition of claim 16, wherein the DNA-binding domain is Gal4.

18. The composition of claim 16, wherein the small molecule hormone-binding domain is derived from a Nuclear Receptor protein.

19. The composition of claim 16, wherein the at least three different affinity tags are Strepll, His and FLAG.

20. The composition of claim 16, wherein the zebrafish inducible promoter is heat, transcription factor or hormone activated.

21. The composition of claim 16, wherein the zebrafish inducible promoter is from the zebrafish hsp70 gene.

22. The composition of claim 16, wherein the reporter protein is selected from the group consisting of green fluorescent protein, red fluorescent protein, DS-red, luciferase, and nuclear, enhanced green fluorescent protein.

23. The composition of claim 16, wherein the first and second nucleic acids are on a single vector.

24. The composition of claim 16, wherein the DNA-binding domain is unlikely to recognize host protein and DNA sequences.

25. The composition of claim 16, wherein each affinity tag provides at least 1000-fold purification with at least 50% yield activity.

26. A method for purifying a modulator of a reporter system, the method comprising:
  (a) providing a zebrafish animal, said zebrafish having the first and second nucleic acids of the composition of claim 1 transiently expressed or incorporated into its genome;
  (b) inducing expression of the first nucleic acid;
  (c) detecting a signal;
  (d) generating a cellular extract from the animal; and
  (e) subjecting the cellular extract generated in step (d) to multiple affinity purification steps, each step comprising binding one affinity tag to an affinity resin capable of selectively binding one affinity tag and eluting the affinity tag from the affinity resin after substances not bound to the fusion protein have been removed.

27. The method of claim 26, further comprising subjecting the purified substance of step (e) to MALDI-TOV, ESI, GC or semi non-denaturing mass spectrometry.

28. The method of claim 26, further comprising after b) contacting the animal with a test compound.

* * * * *